(12) United States Patent
Shah et al.

(10) Patent No.: US 11,553,862 B2
(45) Date of Patent: Jan. 17, 2023

(54) ANALYTE SENSOR

(71) Applicants: PERCUSENNE, Valencia, CA (US); Rajiv Shah, Rancho Palos Verdes, CA (US); Bradley Liang, San Francisco, CA (US); Katherine Wolfe, Mississauga (CA); Ellen Messer, Pasadena, CA (US); Shaun Pendo, Wofford Heights, CA (US)

(72) Inventors: Rajiv Shah, Rancho Palos Verdes, CA (US); Bradley Liang, San Francisco, CA (US); Katherine Wolfe, Mississauga (CA); Ellen Messer, Pasadena, CA (US); Shaun Pendo, Wofford Heights, CA (US)

(73) Assignee: PercuSense, Inc., Valencia, CA (US)

( * ) Notice: Subject to any disclaimer, the term of this patent is extended or adjusted under 35 U.S.C. 154(b) by 479 days.

(21) Appl. No.: 16/625,884

(22) PCT Filed: Jun. 22, 2018

(86) PCT No.: PCT/US2018/038984
§ 371 (c)(1),
(2) Date: Dec. 23, 2019

(87) PCT Pub. No.: WO2018/237259
PCT Pub. Date: Dec. 27, 2018

(65) Prior Publication Data
US 2020/0146596 A1    May 14, 2020

Related U.S. Application Data

(60) Provisional application No. 62/619,078, filed on Jan. 18, 2018, provisional application No. 62/568,293,
(Continued)

(51) Int. Cl.
*A61B 5/1455* (2006.01)
*A61B 5/1486* (2006.01)
(Continued)

(52) U.S. Cl.
CPC ............ *A61B 5/1486* (2013.01); *A61B 5/686* (2013.01); *G01N 33/50* (2013.01); *C12Q 1/001* (2013.01)

(58) Field of Classification Search
CPC ... A61B 5/1486; A61B 5/686; A61B 5/14546; A61B 5/14532; A61B 5/14865; G01N 33/50; G01N 27/3272; C12Q 1/001
See application file for complete search history.

(56) References Cited

U.S. PATENT DOCUMENTS

2012/0190950 A1*  7/2012  Yang ...................... C12Q 1/001
                                                              252/514

FOREIGN PATENT DOCUMENTS

WO          9945387 A2      9/1999
WO          03011131 A2     2/2003
(Continued)

OTHER PUBLICATIONS

International Search Report dated Oct. 10, 2018 for PCT/US2018/038984.

*Primary Examiner* — Marjan Fardanesh
(74) *Attorney, Agent, or Firm* — PercuSense, Inc.

(57) ABSTRACT

An electrode measuring the presence of an analyte is described as one embodiment. The electrode includes a working conductor with an electrode reactive surface and a first reactive chemistry that is responsive to the analyte. The electrode further includes a first transport material that enables flux of the first analyte to the first reactive chemistry and a second transport material that supplies a reactant to the first reactive chemistry. Wherein the first reactive chemistry (Continued)

does not contact the electrode reactive surface while at least partially shadowing a portion of the electrode reactive surface.

20 Claims, 15 Drawing Sheets

Related U.S. Application Data filed on Oct. 4, 2017, provisional application No. 62/524,416, filed on Jun. 23, 2017.

(51) Int. Cl.
*A61B 5/00* (2006.01)
*G01N 33/50* (2006.01)
*C12Q 1/00* (2006.01)

(56) References Cited

FOREIGN PATENT DOCUMENTS

| WO | 2009100082 A1 | 8/2009 |
| WO | 2017196610 A1 | 11/2017 |

\* cited by examiner

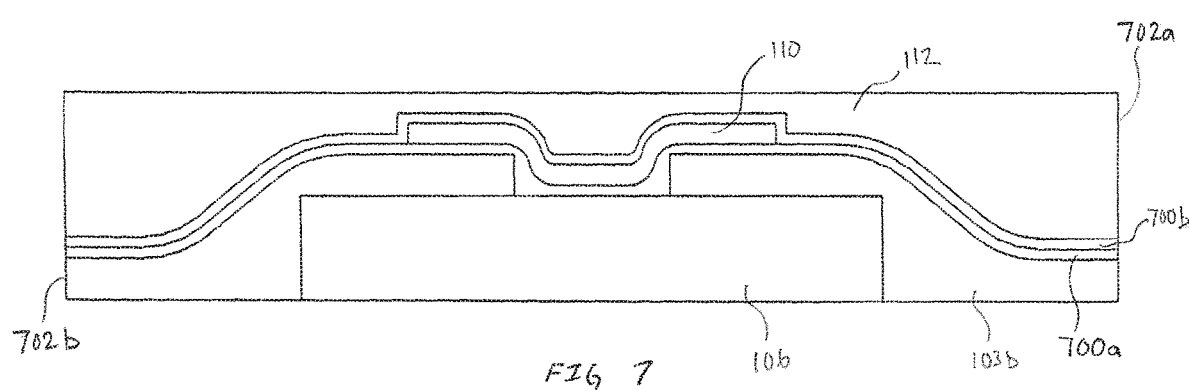

ANALYTE SENSOR

RELATED APPLICATIONS

This application claims the benefit of U.S. provisional application numbers: 62/524,416, filed Jun. 23, 2017; 62/568,293 filed Oct. 4, 2017; and 62/619,078 filed Jan. 18, 2018. The applications listed above are hereby incorporated by reference in their entirety for all purposes.

FIELD OF THE INVENTION

The present invention is generally directed to devices and methods that perform in vivo monitoring of an analyte or analytes such as, but not limited to, glucose or lactate. In particular, the devices and methods are for electrochemical sensors that provide information regarding the presence or amount of an analyte or analytes within a subject.

BACKGROUND OF THE INVENTION

In vivo monitoring of particular analytes can be critically important to short-term and long-term well being. For example, the monitoring of glucose can be particularly important for people with diabetes in order to determine insulin or glucose requirements. In another example, the monitoring of lactate in postoperative patients can provide critical information regarding the detection and treatment of sepsis.

The need to perform continuous or near continuous analyte monitoring has resulted in the development of a variety of devices and methods. Some methods place electrochemical sensor devices designed to detect the desired analyte in blood vessels while other methods place the devices in subcutaneous or interstitial fluid. Both placement locations can provide challenges to receiving consistently valid data. Furthermore, achieving consistent placement location can be critical to hydrating, conditioning and calibrating the device before actual use. Hydrating and conditioning of commercially available sensor devices can be a time consuming process often taking fractions of hours up to multiple hours, to significant fractions of days. Assuming the hydrating and conditioning process is completed successfully, a user may have to compromise their freedom of movement or range of movement in order to keep the sensor properly located within their body.

Glucose sensors are one example of in vivo continuous analyte monitoring. Commercially available implantable glucose sensors generally employ electrodes fabricated on a planar substrate or wire electrodes. In either configuration the electrode surface is coated with an enzyme which is then further coated with a polymer membrane to control the amount of glucose and oxygen that reaches the electrode surface. In some glucose sensors the polymer membrane is hydrophilic which allows glucose to easily diffuse through the membrane layer, however the hydrophilic membrane severely limits the amount of oxygen that can diffuse through the membrane. The lack of oxygen on the electrode surface can become an issue because the glucose sensor works by using the enzyme to catalyze a reaction between glucose and oxygen resulting in hydrogen peroxide that is oxidized at a working electrode. Only when there is an abundance of oxygen present at the working electrode, will the glucose measured by the electrode be proportional to the amount of glucose that reacts with the enzyme. Otherwise, in instances where insufficient oxygen is present at the working electrode, the glucose measurement is proportional to the oxygen concentration rather than the glucose concentration.

Further exacerbating the problem is the deficiency of oxygen relative to glucose in the human body. The ratio of glucose to oxygen in the human body ranges from approximately 10-to-1 to 1000-to-1. This typically means the enzyme catalyzed reaction at the working electrode is generally operating in a condition of oxygen deficiency which can result in many critical problems that influence accuracy, sensitivity and long-term reliability of in vivo sensors. Various approaches have been implemented to counteract the oxygen deficiency problem and increase the relative concentration of available oxygen at the electrode. For example, commercially available glucose sensor systems rely on a highly specialized glucose limiting membrane (GLM) rather than the simply hydrophilic membrane discussed above. Multiple commercial approaches have GLMs that are homogeneous membranes with both hydrophobic and hydrophilic regions to draw in oxygen while also drawing in glucose. One drawback to the implementation of GLMs is the increased cost of the sensor due to the increased cost to manufacture the complex GLMs. Furthermore, material variability within the GLM and non-uniform dispersion of the hydrophilic areas often result in batch to batch variability that affects accuracy, sensitivity and reliability of the sensor. Additionally, because of the hydrophilic and hydrophobic areas of the GLM, diffusion of either glucose or oxygen occurs primarily perpendicular to the surface of the electrode.

Another drawback associated with the use of GLM is that effectiveness of a sensor may be adversely affected if metabolically active cells associated with insertion site trauma or host response interferes with or blocks a portion of the GLM. For example, if red blood cells were to pool in close proximity to the GLM, flow of glucose and oxygen to the sensor electrode could be significantly impeded. Similarly, if white blood cells obstructed flow of glucose across the hydrophilic areas of a GLM the sensor electrode would output erroneous data because glucose that should otherwise reach the working electrode is being consumed by the white blood cells and there is no alternative path for glucose to diffuse to the working electrode.

Another drawback is the hydrophobic nature of GLM. The use of GLM can at least partially explain prolonged hydration and conditioning time for many commercially available glucose sensors. Hydration and conditioning of the sensor requires transportation of fluid to the working electrode. However, because GLM favors the transport of oxygen, the hydrophobic regions of the GLM are placed over the electrode to promote diffusion of oxygen to the electrode. Being hydrophobic, those same areas repel water that is necessary to hydrate the sensor and transport the glucose to the electrode.

The claimed invention seeks to address many of the issues discussed above regarding in vivo monitoring of particular analytes. In many examples discussed below, the analyte being measured is glucose. In still other examples the analyte is lactate. However, while specific embodiments and examples may be related to glucose or lactate, the scope of the disclosure and claims should not be construed to be limited to either glucose or lactate. Rather it should be recognized that the chemistry applied to the electrodes of the sensors described herein is determinative of the analyte the sensor measures.

BRIEF SUMMARY OF THE INVENTION

An electrode measuring the presence of an analyte is described as one embodiment. The electrode includes a working conductor with an electrode reactive surface and a first reactive chemistry that is responsive to the analyte. The electrode further includes a first transport material that enables flux of the first analyte to the first reactive chemistry and a second transport material that supplies a reactant to the first reactive chemistry. Wherein the first reactive chemistry does not contact the electrode reactive surface while at least partially shadowing a portion of the electrode reactive surface.

Other features and advantages of the invention will become apparent from the following detailed description, taken in conjunction with the accompanying drawings which illustrate, by way of example, various features of embodiments of the invention.

DETAILED DESCRIPTION

Figure 1A:
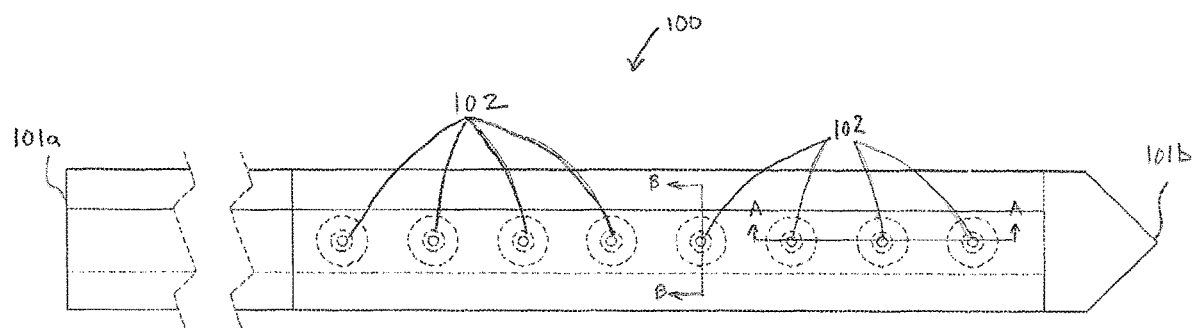
FIG. 1A is a top view of an exemplary sensor assembly having multiple electrodes, in accordance with embodiments of the present invention.

Despite improvements in sensors for in vivo analyte monitoring there are fundamental problems with current designs that adversely affect reliability, accuracy, sensitivity, and durability of in vivo analyte sensors, as discussed above generally in the context of GLMs for glucose sensors. Additionally, many of the designs and processes to manufacture commercially available analyte sensors require the use of precious metals in addition to complicated and complex manufacturing techniques. Described below are designs and manufacturing techniques intended to improve implantable in vivo analyte sensor reliability, accuracy, sensitivity, and durability while driving manufacturing complexity and cost down to enable widespread acceptance and adoption of continuous analyte monitoring.

Theories of operation provided throughout this disclosure should not be considered limiting, rather, the disclosure is being made without being bound by any particular theory of operation. Additionally, throughout the following descriptions and associated drawings, components and elements of electrodes and electrode assemblies will be shown and described in layers. The relative thickness of the layers displayed in the drawings should not be construed as being representative of actual proportions. The relative thickness of the layers discussed throughout this document are intended to be manipulated to improve electrode performance and/or mechanical robustness.

At the working electrode level of a sensor assembly, engineered aspects of the designs presented below enable diffusion pathways that provide access to an excess of reactant to enable complete electrochemical consumption of the product of a chemical reaction. The complete electrochemical consumption of the product of the chemical reaction in turn maintains the condition of mass transfer limitation required for stable and substantially linear sensor response throughout the expected lifetime of a sensor assembly, irrespective of changes in physiological conditions of the subject implanted with the sensor assembly. These improved working electrodes can be implemented with a traditional reference and counter electrode in the traditional three electrode configurations.

Alternatively, the improved working electrode can be combined with an improved pseudo-reference electrode design that includes a low impedance, inert, high surface area electrode that is both directly interfacing with the sensor electrolyte and in galvanic/ohmic contact with an underlying or overlying high surface area, noble metal or electrochemically inert reference electrode that is in electrolytic contact with an external environment surrounding an implanted sensor assembly. The structure of the improve pseudo-reference electrode provides a stable reference potential based on the properties of the underlying reference electrode that is no longer consumed through counter electrode reactions that are now taking place on the overlying high surface area electrode, which enables drift free factory calibrated sensors. Exemplary pseudo-reference electrode designs can be found in U.S. patent application Ser. No. 15/472,194, filed Mar. 28, 2017, which is hereby incorporated by reference in its entirety for all purposes.

Area on the sensor assembly saved by the consolidation of the counter electrode and the reference electrode into a pseudo-reference electrode can be used for placement of embodiments of improved working electrodes to enable multi-analyte sensors. In addition to capabilities discussed above, the improved working electrode designs and the pseudo-reference electrode are able to take advantage of efficient manufacturing processes that enable consistent repeatability required for factory calibration.

The improved working electrode is designed to enable diffusion, transport, or flux of analyte and reactant in dissimilar directions toward a working conductor having an electrode reactive surface. The electrode reactive surface itself can define multiple embodiments. For example, the electrode reactive surface can include, bare, exposed working conductor, or working conductor that has undergone a surface treatment or even working conductor that has a chemistry applied, or combinations thereof. In embodiments where the electrode reactive surface includes a chemistry, a product can be generated by a reaction of an analyte and the chemistry, and the product is substantially, or even completely consumed by an electrochemical reaction with the working conductor. In other embodiments, the analyte is substantially or even completely consumed by an electrochemical reaction with the reactive surface of the working conductor.

The improved working electrode may be referred to as a "floating" electrode because rather than having the reactive chemistry contacting the electrode reactive surface, the reactive chemistry "floats", or is separated from the electrode reactive surface by a layer of first transport material. While the accompanying figures, illustrations and descriptions may include illustrations of electrodes having substantially circular shape, other shapes such as, but not limited to irregular circles, ovals, rectangular or other polygonal shapes can be implemented while staying within the scope of this disclosure. As will become evident in the drawings, a distinguishing characteristic of the floating electrode is the separation of the reactive chemistry away from the electrode reactive surface.

The floating electrode design enables a single or multiple analyte electrochemical sensor comprised of a single, or an array of floating electrodes with an insulation pattern that extends from the surface of the conductor to define an electrode that is recessed within the opening created by the insulation. In embodiments having an array of electrodes, the spacing of the array of electrode elements exceeds the hydrodynamic diameter of the electrode such that the electrode elements operate independently of one another irrespective of whether each electrode element is configured to measure the same or different molecules.

The electrode is subjected to an applied potential that enables the electrochemical oxidation, or reduction, of a molecule that enters the sensor from an external environment, or is formed through a reaction facilitated by, but is not limited to catalyst such as an oxidoreductase enzyme. A transport material covers one or more of the sensor electrode array members thereby establishing a transport pathway between the external environment to be sampled or sensed, and one or more of the sensing electrodes to create a contoured interface between the electrode array element and corresponding insulation layer.

Additionally, a reactive chemistry can be selectively deposited or applied over the electrode, insulation layer, and transport material to partially cover, fully cover, and/or conformally extend over the underlying multilayer structure that includes the electrode, insulation and transport material ensemble. The reactive chemistry may further contain a biorecognition molecule such as, but not limited to an enzyme that imparts sensitivity to the sensor electrode elements to a by-product of the catalytic reaction specific to a molecule of interest that diffuses to the sensor electrode via the transport material.

A second transport material may be conformally applied to the multilayer structure that includes the electrode, insulation, first transport material, and reactive chemistry. In many embodiments the second transport material is hydrophobic. Placed over the first transport material, a hydrophobic second transport material thereby defines both a conduit of first transport material and a no flux boundary that enables a pathway for a water soluble molecule from the external environment to reach the reactive chemistry. Due to the conformality of the multilayer structure the second transport material pathway allows access to the reactive chemistry in a omni-directional matter than is angularly displaced from the direction of entry via the first transport material.

The structure outlined above generally enables the transport of analyte to the reactive chemistry along with electrochemically active by-products of the analyte-reactive chemistry reaction to interact with the longest dimension of either the reactive chemistry or the underlying electrode. Exposure to the longest dimensions of the reactive chemistry and underlying electrode enables complete consumption of analyte and/or reaction by-product, where complete consumption supports the stable mass transfer limited sensor output under conditions of continuous operation that may result in the deactivation or loss of reactive chemistry and electrode functionality. The conformality between the multilayer structure and the second transport material envelopes the reactive chemistry and provides increased interfacial surface area between the second transport material and the underlying reactive chemistry. The increased interfacial surface area enables efficient transport of reactants or other molecules necessary to support the oxidoreductase enzyme reaction in a manner that prevents depletion of the co-reactant of the oxidoreductase enzyme and enables the mass transfer limitation of the molecule to be sensed into the multilayer structure such that the output of the sensor is governed by Fick's law of diffusion which in turn implies that the signal of the sensor is linearly related to the concentration of the molecule within the external environment.

Furthermore, in the absence of a reactive chemistry such as, but not limited to an oxidoreductase enzyme, the multilayer structure defined herein can serve as the basis for a sensor or electrochemically active molecules that can enter the sensor via the first transport material and/or the second transport material to the underlying electrode that may be polarized to oxidize or reduce the electrochemically active molecule of interest.

FIG. 1A is a top view of an exemplary sensor assembly 100 having multiple electrodes 102, in accordance with embodiments of the present invention. The sensor assembly 100 has a proximal end 101*a* and a distal end 101*b*. As this disclosure is primarily directed toward the working electrode the proximal end 101*a* is illustrated without the typical contact pads that enable the sensor assembly 100 to be connected to an electronics package that enables operation and data acquisition, storage and transmission of data acquired by the sensor. The distal end 101b is illustrated as a symmetrical needle point or spear point in order to have the sensor assembly assist during the insertion process. However, in other embodiments the distal end 101b can be alternative shapes, such as, but not limited to chisel tips, compound bevels and a variety of asymmetrical tips that are configured to assist in piercing and cutting during insertion of the sensor assembly.

Shown in dotted lines to illustrate the multilayer structure of the sensor assembly 100, are a plurality of electrodes 102. The specific number of electrodes 102 illustrated in FIG. 1A is intended to be exemplary rather than restrictive. In various embodiments fewer or additional electrodes 102 are formed on the sensor assembly 100. Additionally, the electrodes 102 shown in FIG. 1A are configured to measure a single metric, such as, but not limited to glucose, lactate, reactive oxygen species (ROS), ketones, or oxygen. In many embodiments a single sensor assembly 100 includes multiple sets of working electrodes, each set of working electrodes configured to measure a different analyte or electrochemically active molecule. For example, on a single sensor assembly 100 there may be sets of electrodes configured to measure glucose, lactate and oxygen. In still other embodiments, the types and number of electrodes configured to measure different analytes or metrics is only constrained by the size of the sensor assembly 100 and the size of the electrical traces required for each working conductor.

Figure 1B:
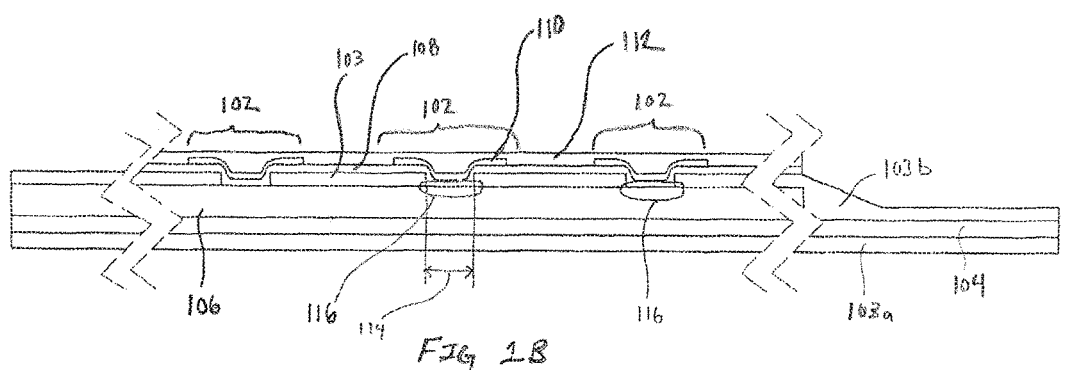
FIGS. 1B-1D are exemplary cross-section illustrations of the multilayer structure of the sensor assembly, in accordance with embodiments of the present invention.
Figure 1C:
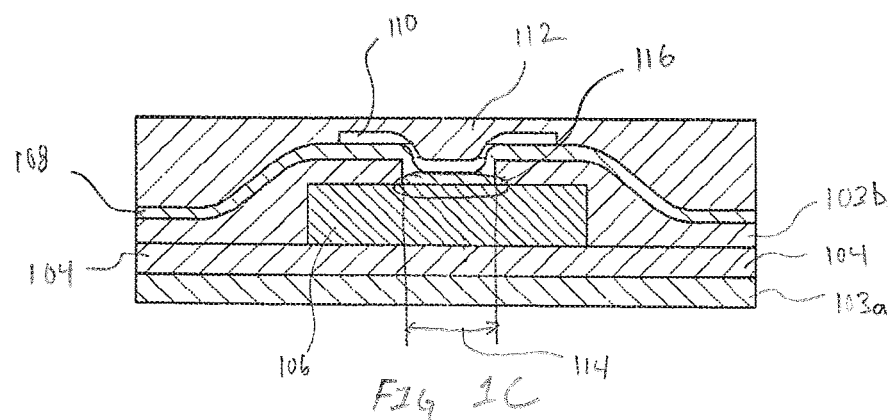
Figure 1D:
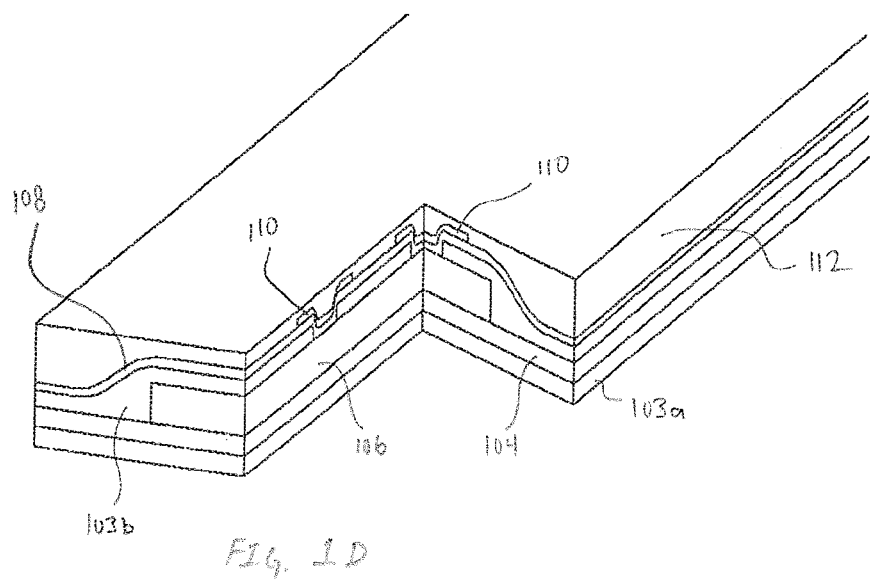

FIGS. 1B-1D are exemplary cross-section illustrations of the multilayer structure of the sensor assembly 100, in accordance with embodiments of the present invention. FIG. 1B is exemplary cross-section A-A of the sensor assembly 100 defined in FIG. 1A. FIG. 1C is exemplary cross-section B-B of the sensor assembly 100 defined in FIG. 1A. FIG. 1D is a pseudo-isometric view of the sensor assembly 100 furthering including a two-way cross-section that further illustrates the three-dimensional nature of the electrode. In each of FIGS. 1B-1D, the sensor assembly 100 can be viewed as a multilayered structure with a base layer being composed of insulation 103a. Adhesive 104 secures the insulation 103a to the working conductor 106. For simplicity, in some figures the insulation 103a and adhesive 104 are combined into a single layer. In these embodiments, the simplified single layer of combined insulation 103a and adhesive 104 is referred to as insulation 103. In other embodiments, the adhesive 104 is optional resulting in a multilayer structure with only insulation 103. An additional layer of insulation 103b is applied over the working conductor 106. In many embodiments the working conductor 106 is selected from a family of stainless steel that are electrically conductive while having mechanical properties of toughness and corrosion resistance that enables cooperative insertion into, and multi-day to multi-week durations within, subcutaneous tissue of a subject.

In many embodiments, sensor assemblies have working conductors 106 for single analyte or multiple analytes are sourced as sheets that includes insulation 103a, adhesive 104, and insulation 103b. In many embodiments the insulation 103a and adhesive 104 are applied to a first side of a conductor and insulation 103b is applied to a side opposite the first side of the conductor. The conductor is imaged to create the working conductor 106 along with other features such as openings 114 in the insulation 103b that expose the electrode reactive surface 116.

In some embodiments the electrode reactive surface 116 is exposed electrical conductor material, such as, but not limited to stainless steel. In other embodiments, the electrode reactive surface 116 is processed to enhance mechanical and electrical properties. In some embodiments processing of the electrode reactive surface 116 applies a material that is a noble metal or other electrochemically inert substance that increases the surface area of the electrode reactive surface. Another highly desirable attribute of processing the electrode reactive surface 116 is increasing the porosity. Accordingly, in many embodiments the processing of the electrode reactive surface 116 includes, but is not limited to, electrochemical plating of materials or combinations of materials such as silver, silver/silver-chloride, platinum black and the like onto the exposed working conductor 106. In many embodiments a the working conductor 106 exposed in the openings 114 undergoes a first processing operation that applies a seed layer. Additional processing can apply additional layers of like or different material over the seed layer.

An alternate non-limiting exemplary embodiment includes application of materials such carbon over the exposed working conductor 106 or alternately, over an electrochemically processed electrode reactive surface 116 to improve, enhance or tune the electrical properties of the electrode. In embodiments where the material being applied to the exposed working conductor 106 may not readily be applicable via electroplating, techniques such as, but not limited to screen printing and vapor deposition can be utilized to apply the material. Regardless of whether the electrode reactive surface 116 is processed or bare working conductor 106, a subsequent layer of first transport material 108 is applied across the surface of the insulation 103a and electrode reactive surface 116.

As illustrated in FIGS. 1B-1D, the first transport material 108 blankets the insulation 103b and electrode reactive surface 116 and extends to every exposed edge of the sensor assembly 100. In preferred embodiments, the first transport material 108 is selected from a family of hydrogels that enables the transport of the molecule or molecules to be measured, such as analytes or other biomarkers within a subject. For example if the electrodes 102 are configured to measure glucose, the first transport layer 108 would be selected based on its ability to enable the transportation or diffusion of glucose. In embodiments enabling multi-analyte sensing, the first transport layer 108 may be selected based on the ability to transport all of the analytes being measured. Alternatively, in some embodiments, multiple layers of different transport layers can be applied. In still other embodiments, mixtures, blends or other combinations of hydrogels can be combined to make a first transport material capable of enabling diffusion of all the desired analytes and/or molecules.

Further elaborating on a glucose sensor embodiment, the selection of the first transport material would enable substantially omnidirectional transportation of glucose, and in some embodiments the preferred first transport material is selected from a hydrophilic family of hydrogel materials. Specifically, three-dimensional hydrogels that mimic or replicate glucose transport in and around islet cells. Because the selected three-dimensional hydrogel mimics or replicates glucose transport in and around islet cells, the hydrogel pathway to the electrode enables glucose conditions within a subject to be substantially replicated within the electrode structure. This is entirely different than with sensors utilizing GLM. As is described by the name of the material itself, glucose limiting membrane, glucose conditions within a subject are intentionally not replicated within the electrode structure utilizing GLM because the GLM favors the movement of oxygen and intentionally limits the movement of glucose.

An additional benefit of using hydrogels to transport analytes is the ability to tune, manipulate, or design diffusion pathways to achieve factory calibration of the electrode. Factory calibration can be understood as an electrode where in vitro data substantially correlates with in vivo data across an entire operating range without the use of a calibration or correction factor. In essence, without the use of correction factors or calibration factors, factory calibration results in in vivo measurements being substantially the same as in vitro measurements. Because the three-dimensional hydrogel pathway to the electrode structure mimics islet cells, glucose concentrations within the electrode structure are expected to approximate glucose concentrations outside the electrode regardless of whether the electrode is placed in vivo or in vitro. Additionally, because the three-dimensional hydrogel is hydrophilic, electrode designs implementing three-dimensional hydrogels rather than GLM should demonstrate faster stabilization and hydration.

While specific embodiments of the first transport material have been described in detail, the exemplary embodiments should not be construed as limiting. In other embodiments, the first transport material can be selected based on properties of analytes found in blood, muscle, or specific organ tissue or other biomarker containing fluids. The use of hydrogels as the first transport material, while perfectly suitable for glucose and other water soluble molecules, may be inappropriate or less than ideal for other biomarker molecules capable of being measured using the electrode. Accordingly, the disclosure should be interpreted broadly as encompassing any materials that enable diffusion of desired molecules or compounds to the electrode.

A first reactive chemistry 110 is applied over the first transport material 108. An alternate name for the first reactive chemistry 110 is a first biorecognition layer because the first reactive chemistry can be selected from a family of oxidoreductase molecules that react with the molecule being detected. Exemplary oxidoreductase molecules include families such as, but not limited to oxidases and dehydrogenases. Specific non-limiting example of specific oxidases and dehydrogenases that react with molecules being detected include glucose oxidase/dehydrogenase and lactate oxidase/dehydrogenase. As illustrated in FIGS. 1B-1D the first reactive chemistry 110 is selectively applied over the opening 114. In embodiments where the openings 114 are circular, it may be preferred that the first reactive chemistry 110 is applied substantially concentric with the opening 114 and the first reactive chemistry extends beyond the opening 114. In embodiments utilizing openings other than circular, it may be preferable to have the first reactive chemistry 110 applied to obfuscate or substantially shadow the opening 114 while also extending beyond the opening 114. As illustrated in subsequent embodiments, extending the first reactive chemistry beyond the opening 114 may not be necessary. In some embodiments, it may be desirable to have the application of the first reactive chemistry 110 remain within the opening 114 while still at least partially shadowing the electrode reactive surface. The shape of the openings 114 and the shape of the first reactive chemistry 110 is exemplary. In various embodiments the openings 114 and the first reactive chemistry 110 may be either similar or different. Regardless of shape, the first reactive chemistry 110 is applied on top of the first transport layer 108 resulting in many embodiments where the first reactive chemistry 110 is substantially conformal to the existing first transport layer 108 and opening 114. In other embodiments, the first reactive chemistry 110 is applied resulting in a substantially flat interface with the subsequently applied second transport material 112. Non-limiting examples of first reactive chemistry 110 includes, but is not limited to oxidoreductase enzymes such as glucose oxidase, lactate oxidase and other enzymes that utilize NADP or NAD+ as cofactors.

Covering the first transport material 108 and the first reactive chemistry 110 is a second transport material 112. In many embodiments, the second transport material 112 is selected from a family of silicone materials that is impervious or impermeable to the analyte or analytes or other biomarkers being measured by the electrodes 102. Because the second transport material 112 is impermeable to the various analytes and biomarkers, the sole pathway for analyte or biomarkers to reach the electrode is through the first transport layer 108. In some embodiments it may be advantageous to pattern the second transport materials 112 to enable pathways for analyte flux. In an embodiment configured to measure glucose, with the first transport material enabling a supply of glucose to the reactive chemistry, the second transport material is chosen based on its ability to supply a reactant complementary to glucose in the presence of the reactive chemistry. Accordingly, if the reactive chemistry being used is glucose oxidase, the second transport material can be selected based on its ability to transport and supply oxygen.

Consequently, in such embodiments, the second transport material is selected from a family of materials, such as, but not limited to silicone. Using silicone as the second transport material provides oxygen to the glucose oxidase reaction and helps to enable and sustain linearity when using oxidase based materials for the first reactive chemistry 110. The specific embodiments described above regarding the second transport materials 112 are intended to be exemplary and should not be construed as limiting. Selection of the second transport materials should not be bound by this disclosure so much as the specific properties of the materials being used to create the desired electrode. Embodiments of the sensor assembly 100 can be single analyte where a single working conductor has a plurality of electrodes 102. Similarly, a multi-analyte sensor is enabled by combining a plurality of single working conductor having at least one electrode 102, each working conductor having a first reactive chemistry selected to measure different analytes or biometrics.

Figure 1E:
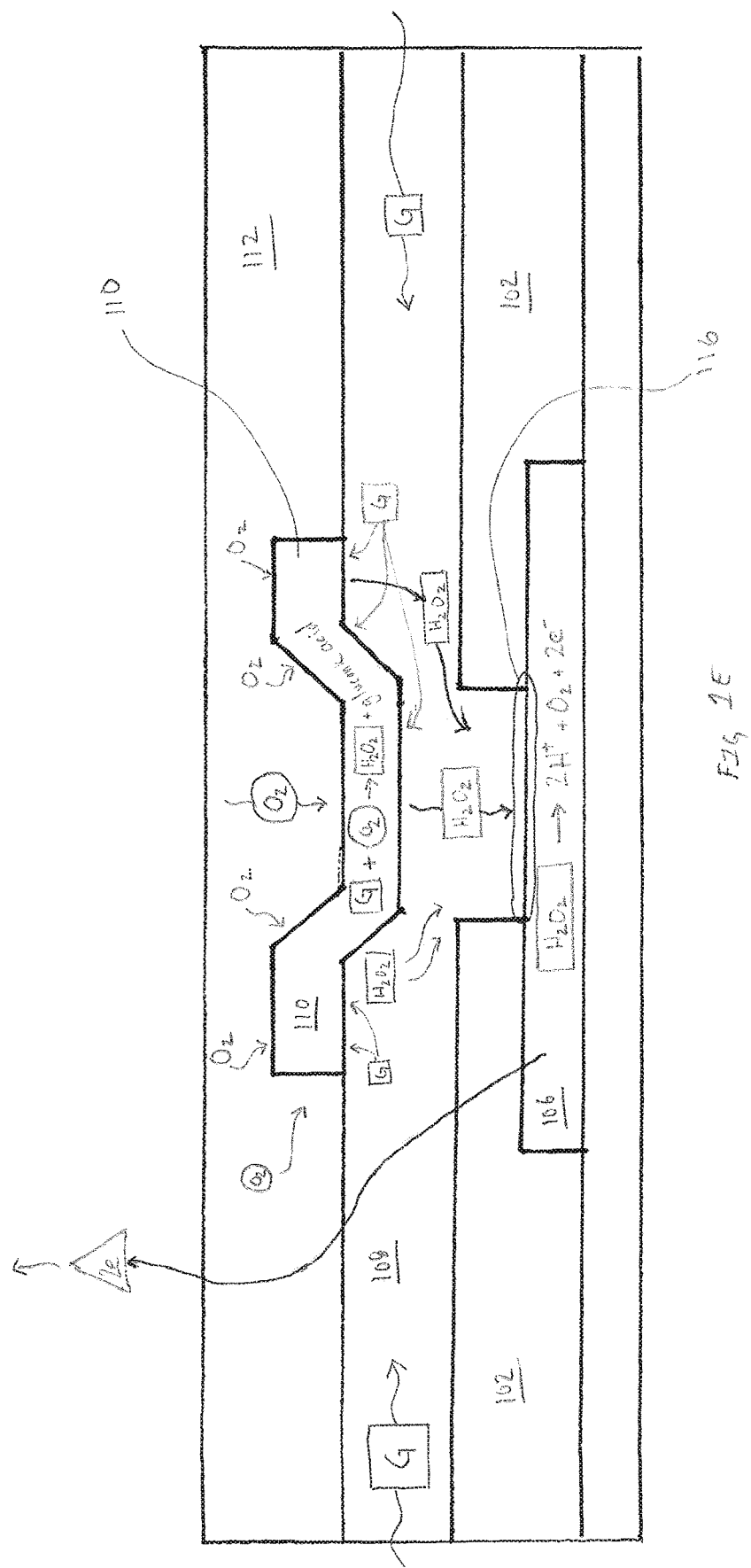
FIG. 1E is an exemplary cross-section illustration of the sensor assembly further showing flux of analyte, reaction by-product and reactant within the sensor assembly, in accordance with embodiments of the present invention.

FIG. 1E is an exemplary cross-section illustration of the sensor assembly 100 illustrating diffusion of analyte, reactant and reaction by-product within one electrode 102 of the sensor assembly 100, in accordance with embodiments of the present invention. The embodiment illustrated in FIG. 1E is based on the use glucose oxidase as the first reactive chemistry 110 thereby enabling the electrode 102 to generate hydrogen peroxide that correlates to the concentration of glucose based on the following chemical reaction:

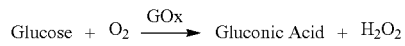

$$\text{Glucose} + O_2 \xrightarrow{\text{GOx}} \text{Gluconic Acid} + H_2O_2$$

Upon insertion of the sensor assembly into a subject concentration of analytes (glucose in this embodiment) and other biomarkers around the sensor will be higher than within the individual electrodes of the sensor assembly. Concentrations of analytes and biomarkers will attempt to achieve equilibrium within the first transport materials 108 of the sensor resulting in glucose from the fluid surrounding the sensor assembly being drawn into the first transport layer 108. Recall that fluid surrounding the sensor assembly can enter the sensor via the hydrophilic first transport material 108 but fluid cannot enter through the hydrophobic second transport material 112. In FIG. 1E glucose, represented as a G within a square, is shown entering the first transport material 108. Furthermore, oxygen, represented as $O_2$ is shown being supplied from the second transport materials 112 to the first reactive chemistry 110. The glucose and oxygen react with the first reactive chemistry 110 according to the chemical reaction described above resulting in the creation of by-products gluconic acid and hydrogen peroxide. The by-product hydrogen peroxide, shown as $H_2O_2$ in FIG. 1E, is transported via the first transport material 108 to the electrode reactive surface 116 where an applied electrical potential reduces it based on the following reaction:

$$H_2O_2 \rightarrow 2H^+ + O_2 + 2e^-$$

where the $2e^-$ is the electrical current picked up by the counter electrode. The consumption of glucose within the electrode lowers the concentration of glucose within the first transport layer establishing a diffusion gradient that strives to reach equilibrium by bringing in additional glucose from the fluid surrounding the sensor assembly.

When compared to traditional glucose sensors that utilize GLM the electrode illustrated in FIG. 1E is easily identifiable as different in that the first reactive chemistry 110 is physically separated from the electrode reactive surface 116 by the first transport materials 108. The physical separation of the first reactive chemistry 110 from the electrode reactive surface 116 requires specific selection of the first transport material to support fundamental changes to diffusion within the electrode. For example, the first transport material 108 must support diffusion of the desired analyte in addition to the by-product of the analyte and the first reactive chemistry. Furthermore, in many embodiments it is desirable that the first transport material 108 also enables diffusion of the by-products of the electrochemical reaction occurring at the electrode reactive surface 116.

Placement of the first transport material 108 over the opening 114, and subsequent placement of the first reactive chemistry over the first transport layer 108 moves the enzymatic reaction between analyte and first reactive chemistry 110 away from the electrode reactive surface 116. The separation of the enzymatic reaction and the electrochemical reaction reduces or minimizes the likelihood of localized pH fluctuations that accompany the electrochemical reaction that can have a negative impact on the first reactive chemistry 110. An additional benefit of the floating electrode is the first transport material 108 pathway that extends completely under the first reactive chemistry 110 that enables laterally diffusing analyte to be transported under and across the longest surface of the first reactive chemistry 110. After the enzymatic reaction, the by-product of the enzymatic reaction is consumed by the electrochemical reaction occurring on the electrode reactive surface 116. Accordingly, with hydrogen peroxide producing enzymatic reactions, the first transport material 108 pathway separating the electrode reactive surface 116 and the first reactive chemistry 110 enables analyte and by-products of the enzymatic reaction to move in substantially opposite directions.

An additional benefit of placing the first reactive chemistry 110 between the first and second transport materials 108/112 is improved manufacturability. In many embodiments the first reactive chemistry 110 is a mixture, blend or suspension of a specific enzyme, or biorecognition molecule, within a second material such as, but not limited to, the first transport material. Thus, applying the first reactive chemistry 110 over a layer of the first transport material 108 improves manufacturability because like materials are being placed on like materials.

Figure 1F:
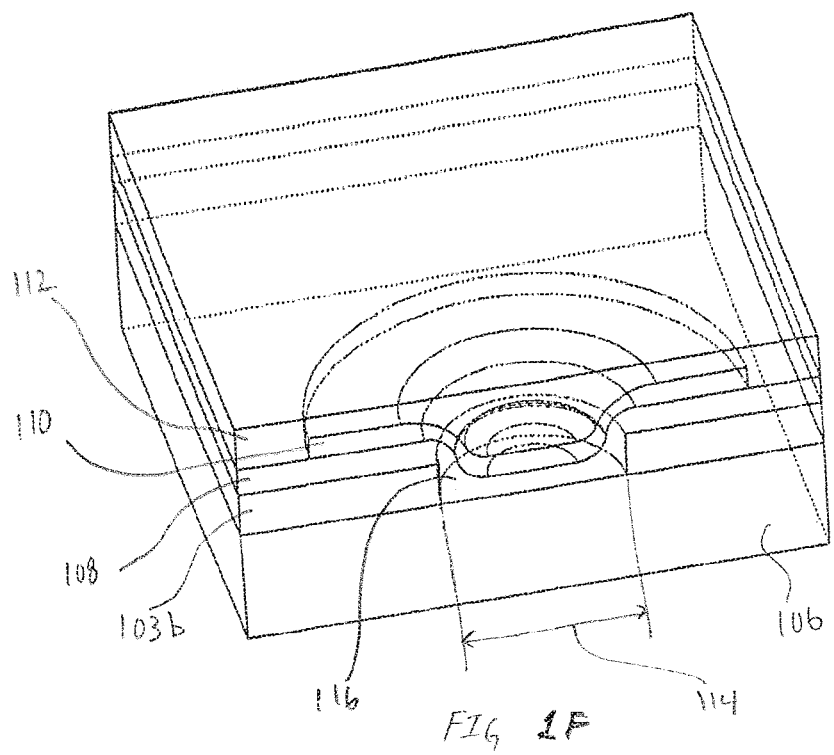
FIGS. 1F and 1G are exemplary pseudo-isometric views illustrating the three-dimensional topography of the electrode, in accordance with embodiments of the present invention.
Figure 1G:
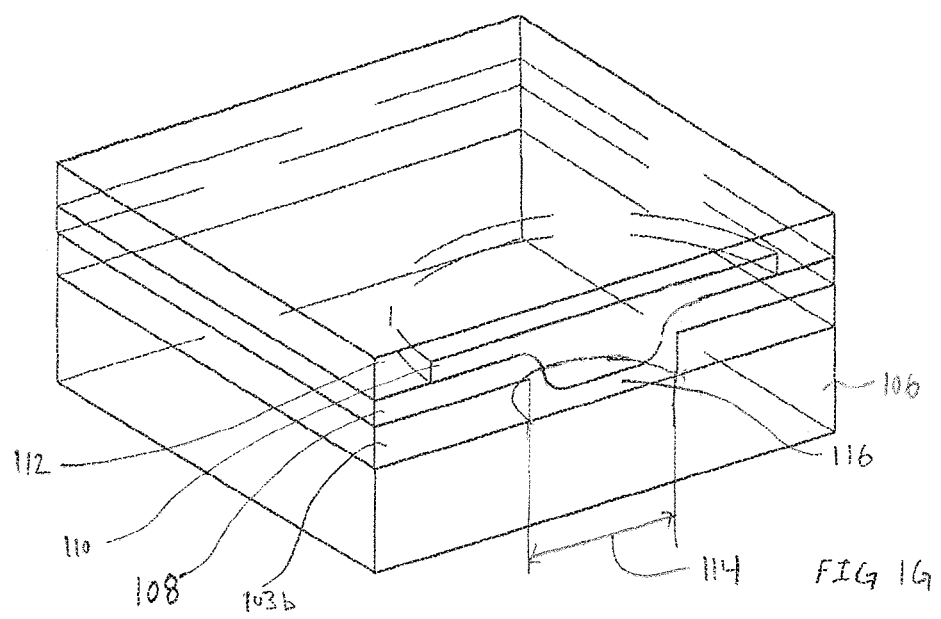

FIGS. 1F and 1G are exemplary pseudo-isometric views illustrating the three-dimensional topography of the electrode 102, in accordance with embodiments of the present invention. The embodiment illustrated in FIGS. 1F and 1G includes a circular opening 114. However, in FIG. 1F the application of the first reactive chemistry 108 results in a depression centered around the opening 114. Contrasted with the embodiment in FIG. 1G where the first reactive chemistry 108 has been applied resulting in a substantially flat surface. Though the two different embodiments are substantially the same, one benefit of the embodiment in FIG. 1F is the more uniform thickness of the first reactive chemistry 108. The more uniform thickness of the first reactive chemistry 108 can enable more rapid diffusion of reactant from the second transport material 112 to a reactive surface of the first reactive chemistry 110. When viewed in the pseudo-isometrics, the ability of second transport material 112 to supply reactant across the entirety of the surface of the first reactive chemistry 110 becomes evident. With the present invention the diffusion of reactant from the second transport material 112 is enabled across 360 degrees of the exposed surface of the first reactive chemistry 110 and further along the exposed edge of the first reactive chemistry 110. This results in the first reactive chemistry 110 essentially being bathed in reactant that may be very beneficial in sustaining the enzymatic reaction depending on the type of first reactive chemistry 110.

Figure 1H:
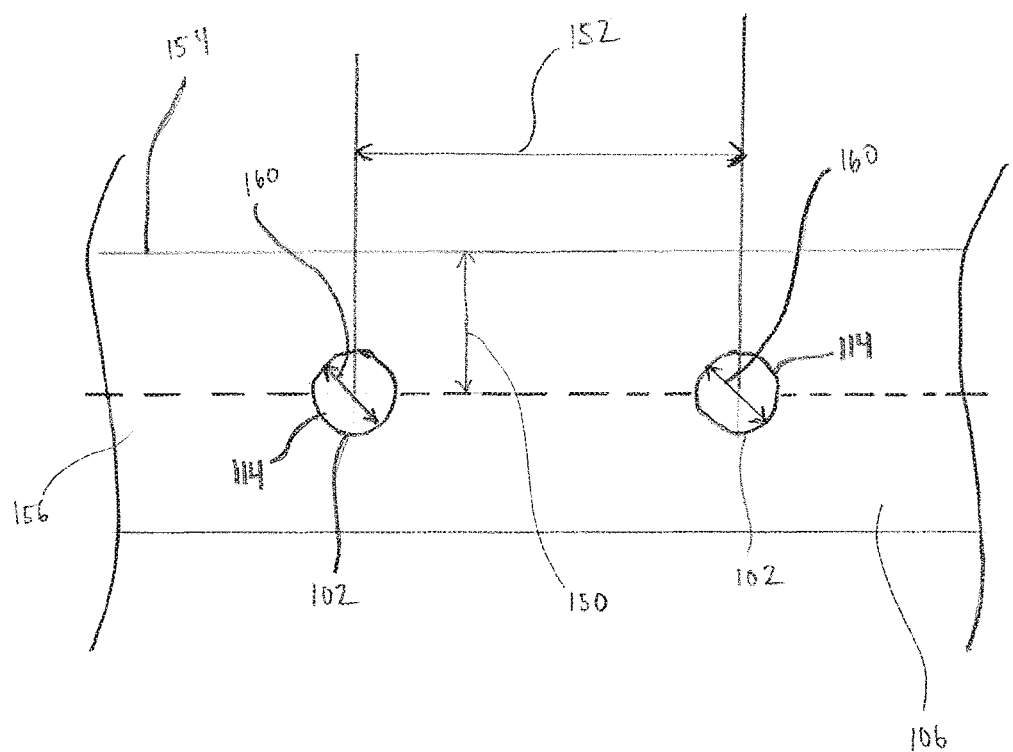
FIG. 1H is an exemplary not-to-scale top view of a portion of a patterned working conductor that includes callouts identifying various dimensions between features that are incorporated into a sensor assembly, in accordance with embodiments of the present invention.
Figure 1L:
FIG. 1I is an exemplary cross-section illustrating the structure of a pseudo-reference electrode resulting from processing exposed electrode reactive surface on a pseudo-reference conductor, in accordance with embodiments of the present invention.
FIG. 1J is an exemplary sensor assembly illustrating ionic flux between a working electrode within an array of working electrodes and the pseudo-reference electrode formed on a opposite side, in accordance with embodiments of the present invention.

FIG. 1H is an exemplary, not-to-scale, top view of a portion of a patterned working conductor 106 that includes callouts identifying various dimensions between features that are incorporated into a sensor assembly 100, in accordance with embodiments of the present invention. FIG. 1H is intended to enable discussion of how relative placement and size of features enables and enhances performance of the sensor assembly 100. The exemplary portion of working conductor 106 includes two opening 114, each opening 114 having a diameter 160. The centers of the openings 114 are created along a centerline of the working conductor 106 that is a distance 150 from an edge 154. Furthermore, the openings 114 are spaced center-to-center at a spacing distance 152.

Application of the subsequent layers enables a mass transfer limited analyte sensor for in-vivo or implantable applications consisting of a plurality of surfaces disposed over three-dimensions that support the partitioning and diffusion of analyte and by-products into a sensor having an array of reactive chemistry or chemistries and corresponding electrode structures. In many embodiments the surface area for analyte and by-product diffusion (the first transport material) is in significant excess of the surface area of reactive chemistry. The area of reactive chemistry and electrode reactive surface, exposed as opening 114, is composed of an array of conformal reactive chemistry discs (discs placed over circular openings in this embodiment) that are discrete and discontinuous. Each of the openings 114 have a diameter 160 and are separated by at least spacing distance 152. Reactive chemistry, separated from the openings 114 by first transport materials conformally overlays and shadows the openings 114. The reactive chemistry may coincide, overlap or be within the opening perimeter resulting in the nominal separation between reactive chemistry being substantially equal to, less than, or more than separation distance 152 between the openings 114.

The center of each opening 114 and overlying conformal reactive chemistry is separated from the edge of the sensor, or the location where analyte partitioning into the sensor occurs, by distance 150. Where distance 150 is substantially larger than diameter 160 thereby imparting the primary mechanism for the mass transfer resistance necessary for a mass transfer limited sensor. Furthermore, the surface area for analyte partitioning, defined at distance 150, or the surface area of the first transport layer at the edge of the sensor assembly, far exceeds the surface area available for analyte reaction calculated via the summation of the surface area of the discontinuous elements of reactive chemistry and corresponding electrode structure. This ratio restricts the consumption of analyte and co-reactant in order to establish the mass transfer limited transport of analyte.

In some embodiments, the overabundance of co-reactant required by the discontinuous elements of reactive chemistry and electrode structure is provided by transport or diffusion of co-reactant into each of the first reactive chemistry through multidimensional transport of co-reactant via the second transport material. The second transport material being in intimate contact with the first reactive chemistry and further being both permeable to the co-reactant while being highly impermeable or impervious to the molecule being measured, or the analyte. The resulting diffusive flux of analyte into the sensor begins at the edge of the sensor, which represents the minimum distance between analyte entry or partitioning into the sensor, may be symmetric with respect to the first reactive chemistry and corresponding electrode structure. In alternative embodiments, the minimum distance between the edge of the sensor and the first reactive chemistry may be asymmetric as long as distance 150 represents the minimum distance from the location of analyte entry and the nearest location of first reactive chemistry. In asymmetric embodiments the molecule being measured establishes concentration gradients based on relative distance to the edge of the sensor assembly. For example, if the first reactive chemistry is biased to one edge, thereby creating a short side and and a long side having higher concentration of analyte on the short side, and lower concentration of analyte on the long side. However, because the higher concentration of analyte is able to move across and around the first reactive chemistry via the first transport material the different diffusion gradients associated with asymmetric placement of the openings and electrodes result in minimal or negligible impact on sensor performance.

In many embodiments, the pathway of analyte into the sensor via the first transport material enables a phenomenon of analyte flux concentration. The concentration of analyte flux is due to the exposed area of the first reactive chemistry and corresponding electrode structure being substantially lower than the area of analyte partitioning and that analyte consumption occurs across an array of structures having approximately diameter 160 separated by a sufficient separation distance 152 to prevent or avoid depletion of analyte between the discrete discs of first reactive chemistry and corresponding electrode structure. This further enables the establishment of independent mass transfer limitation to each disc of first reactive chemistry which in turn leads to a composite but independent mass transfer limitation across the entire array of sensing elements which in turn imparts the overall property of mass transfer limitation to the sensor described herein and thus a sensor that responds linearly to the analyte of interest and in a manner prescribed by Fick's law of diffusion.

Note that the use of equally sized circular openings 114, spaced along a centerline having a spacing distance 152 having a diameter 160 are intended to be exemplary. Other embodiments include, but are not limited to openings having various to varying shapes and sizes formed on a single sensor assembly. Additionally, the variously shaped and sized openings can be located at varying distances from the edge of the sensor assembly and further include varying spacing distance 152 between openings 114.

Figure 1J:
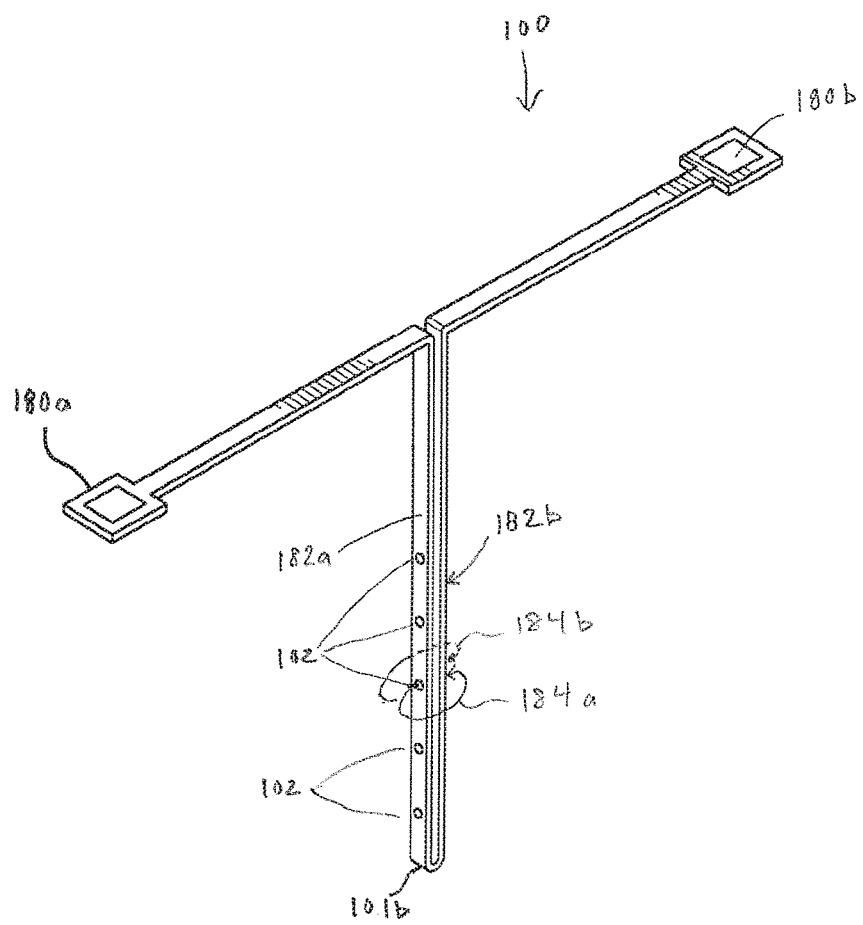
Figure 1A:
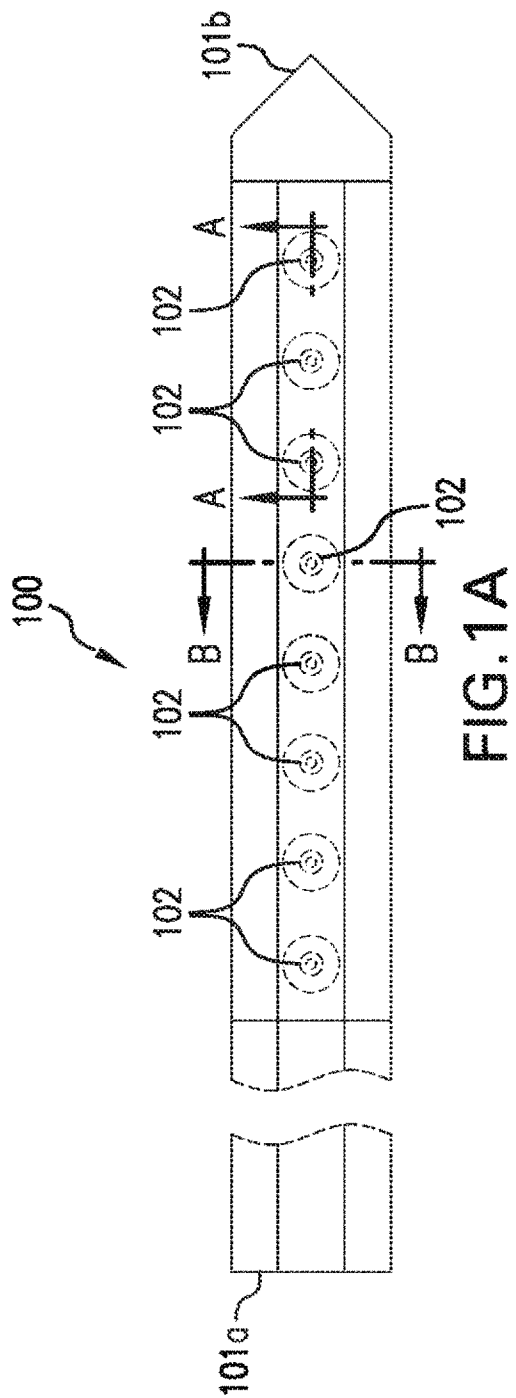
Figure 1B:
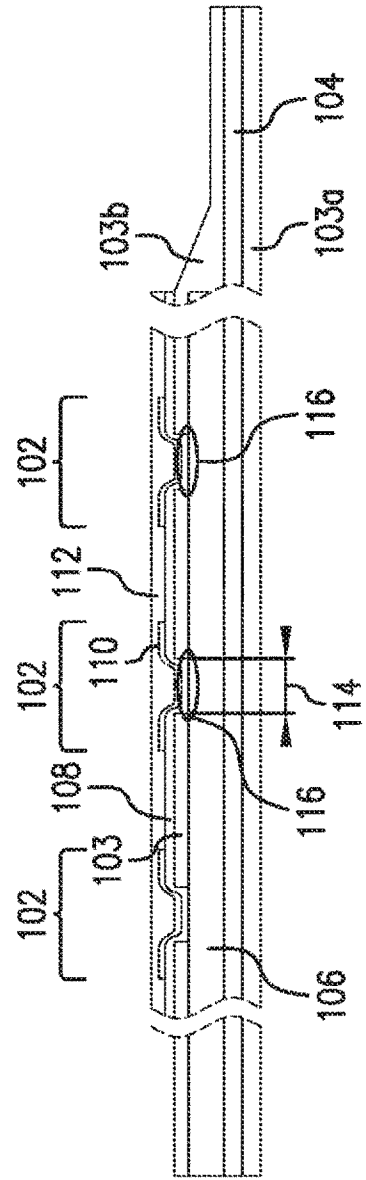
Figure 1C:
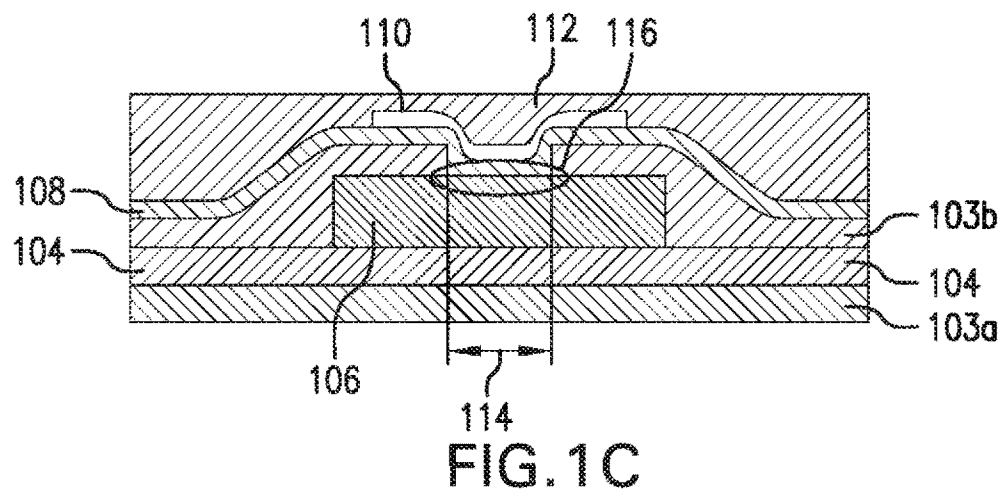
Figure 1D:
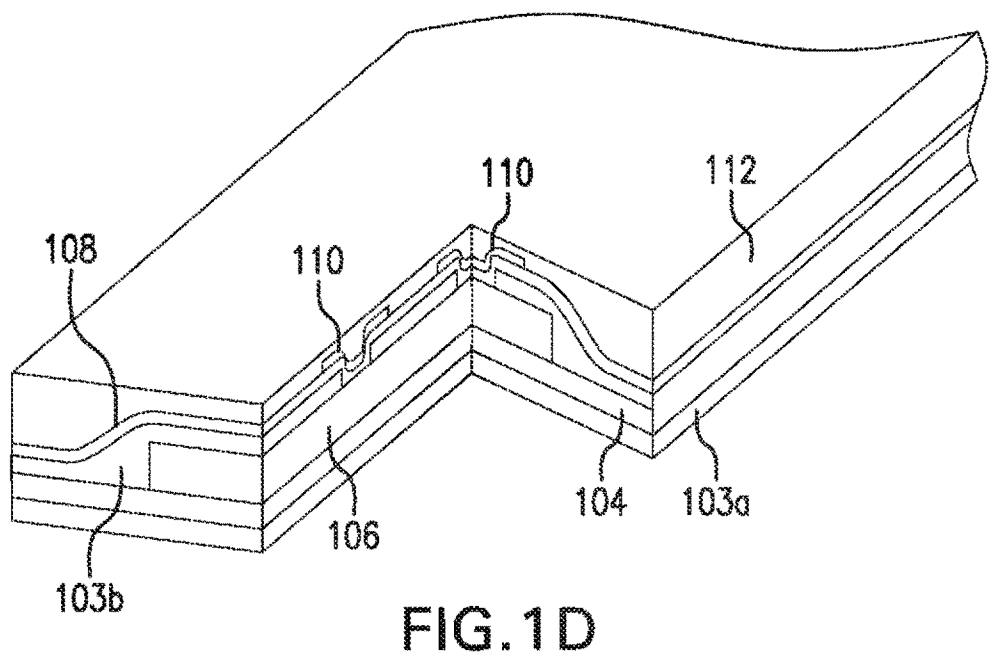
Figure 1E:
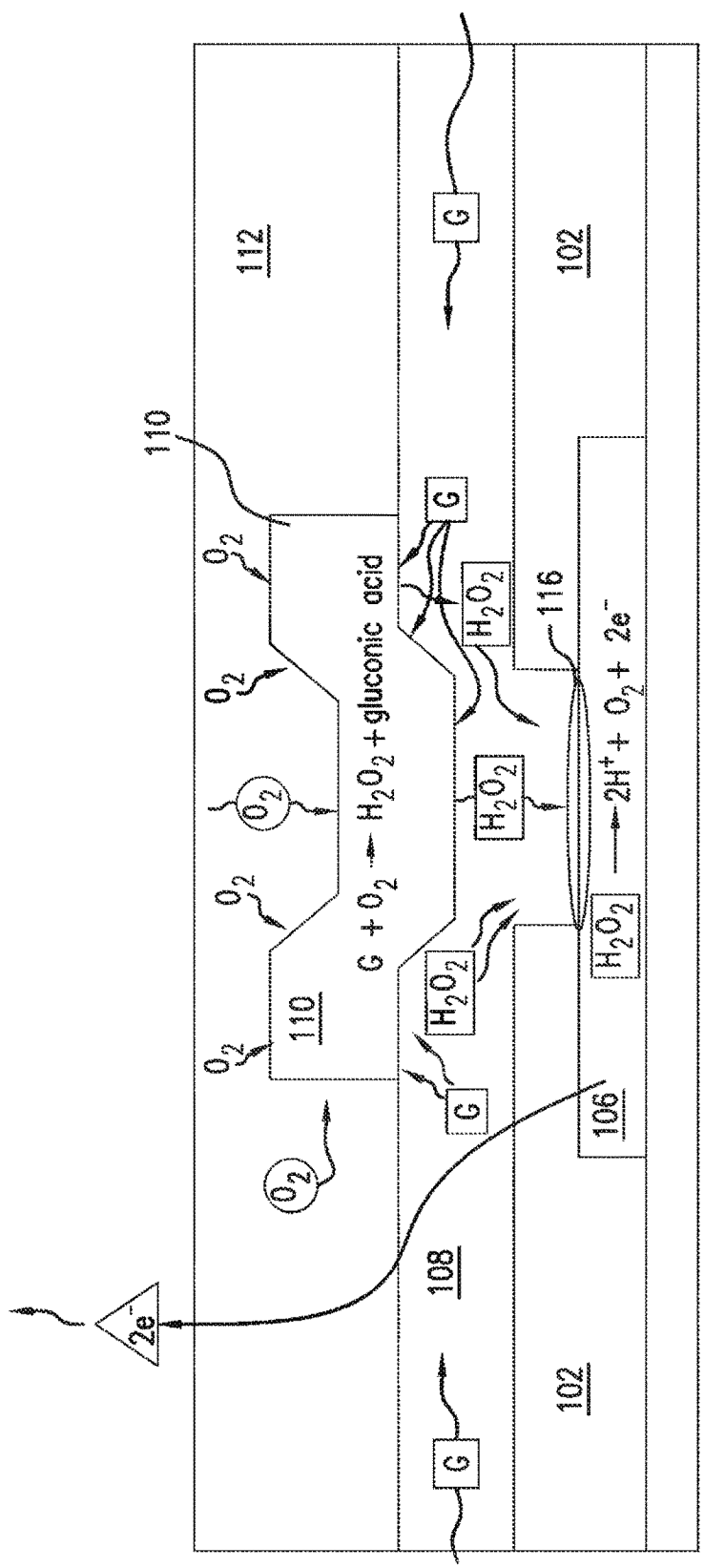
Figure 1F:
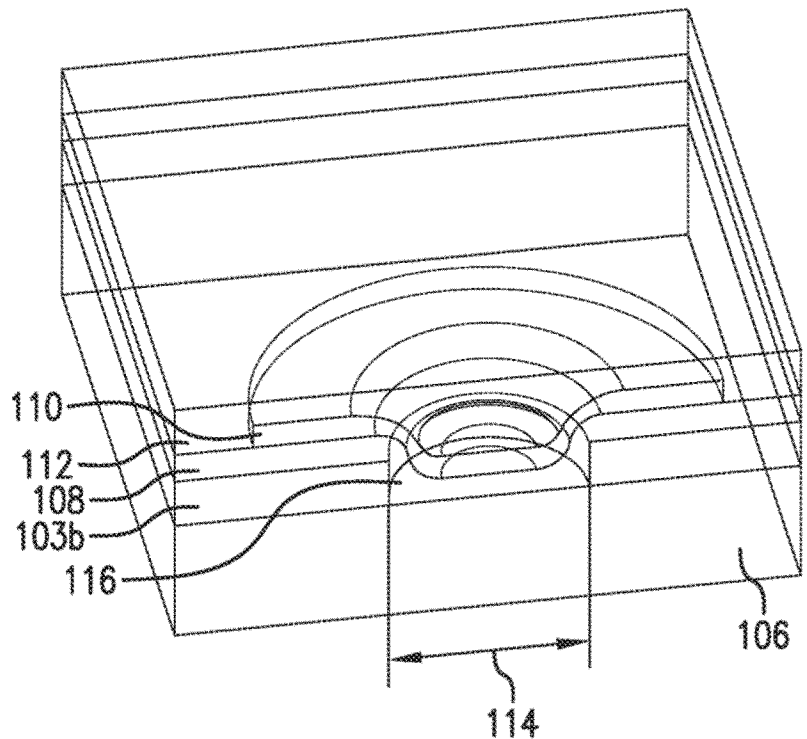
Figure 1G:
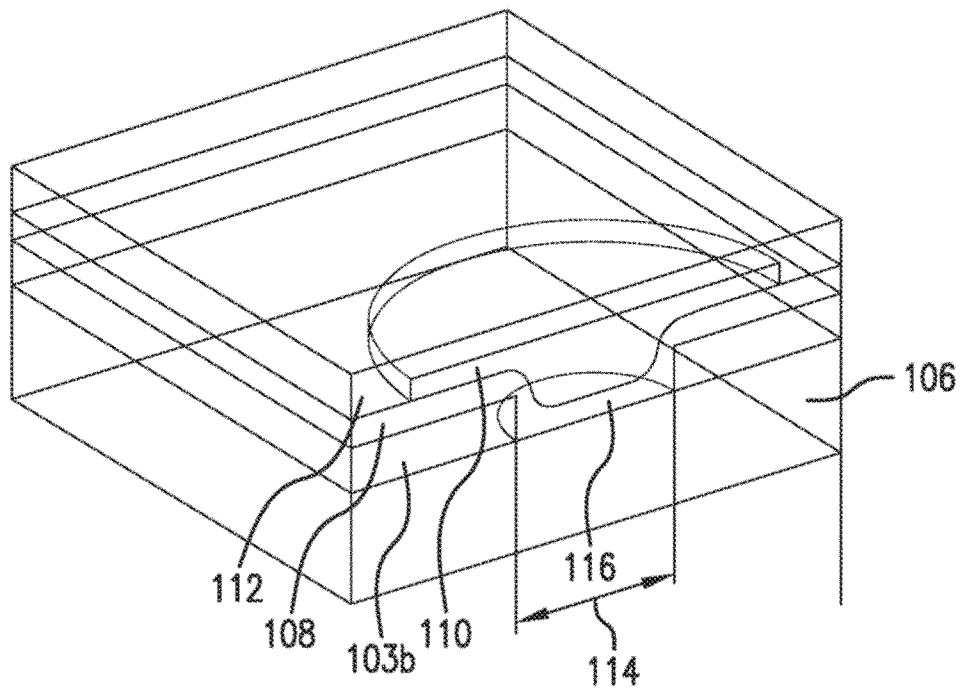
Figure 1H:
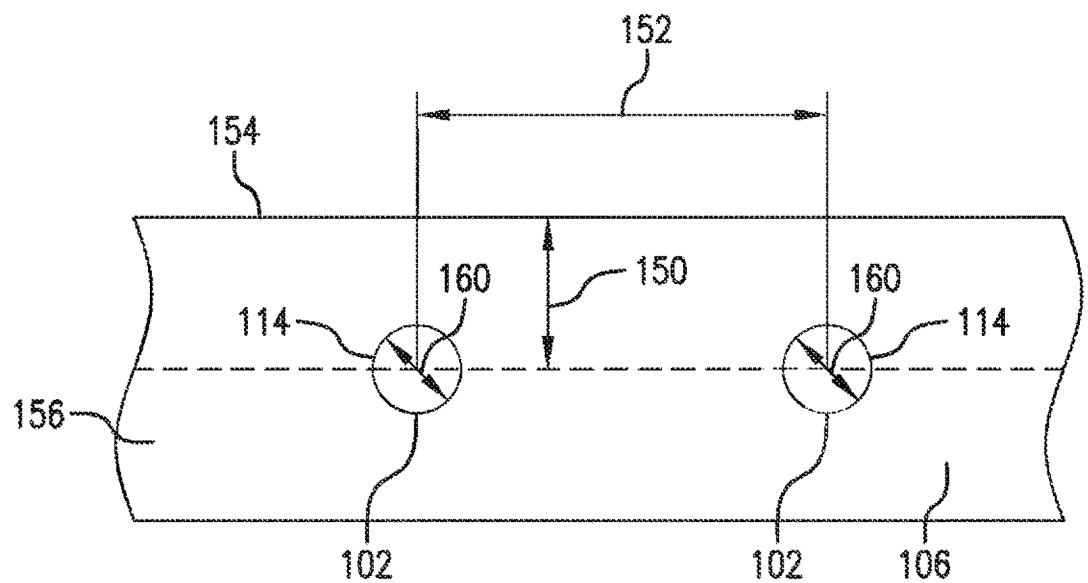
Figure 1I:
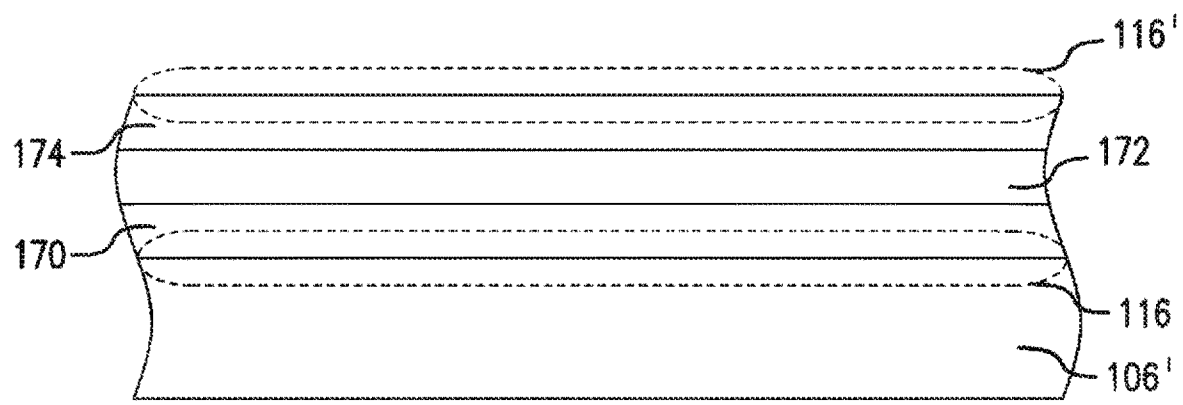
Figure 1J:
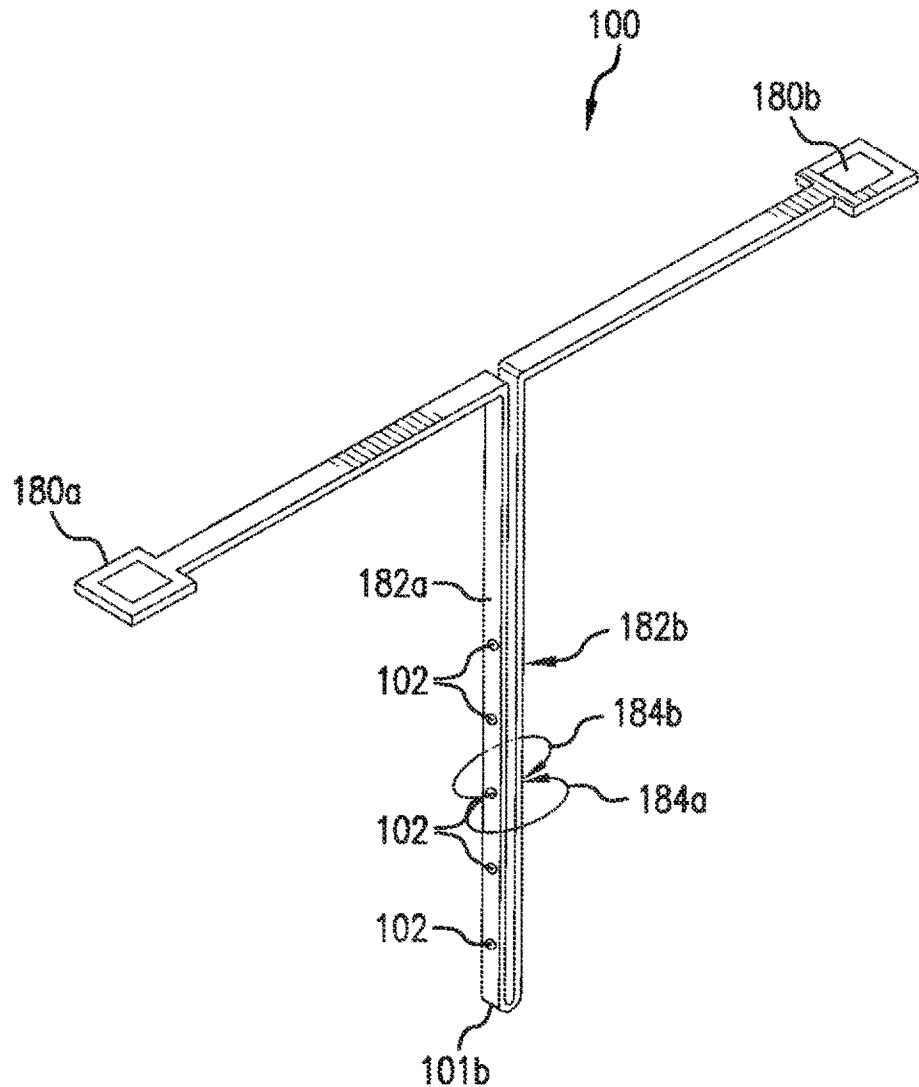
Figure 2A:
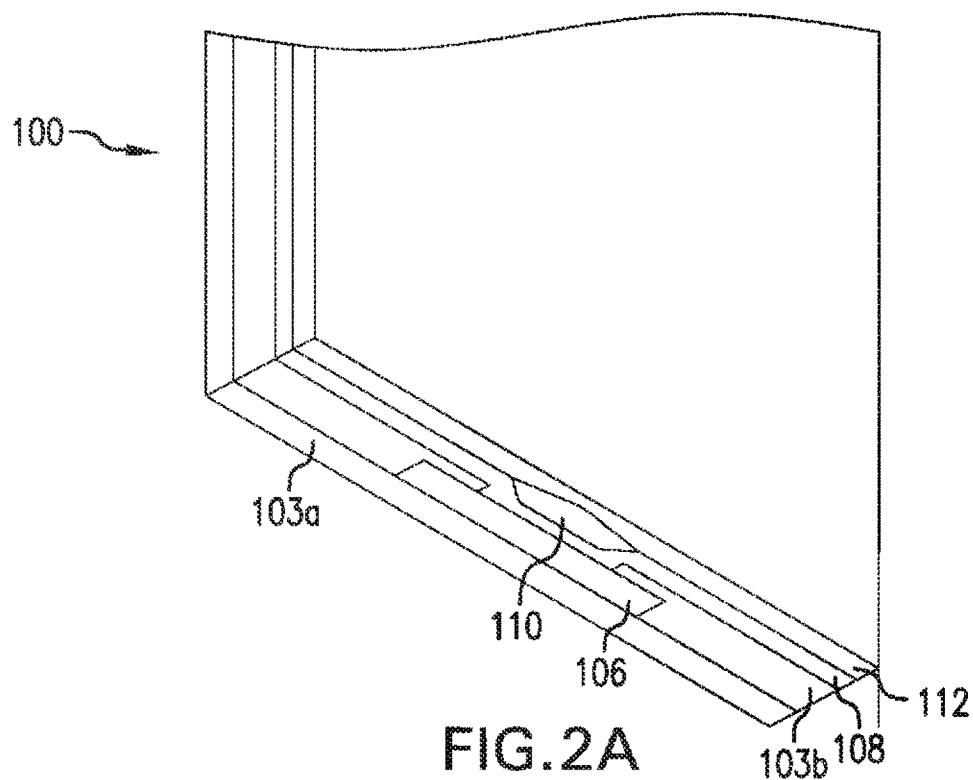
Figure 2B:
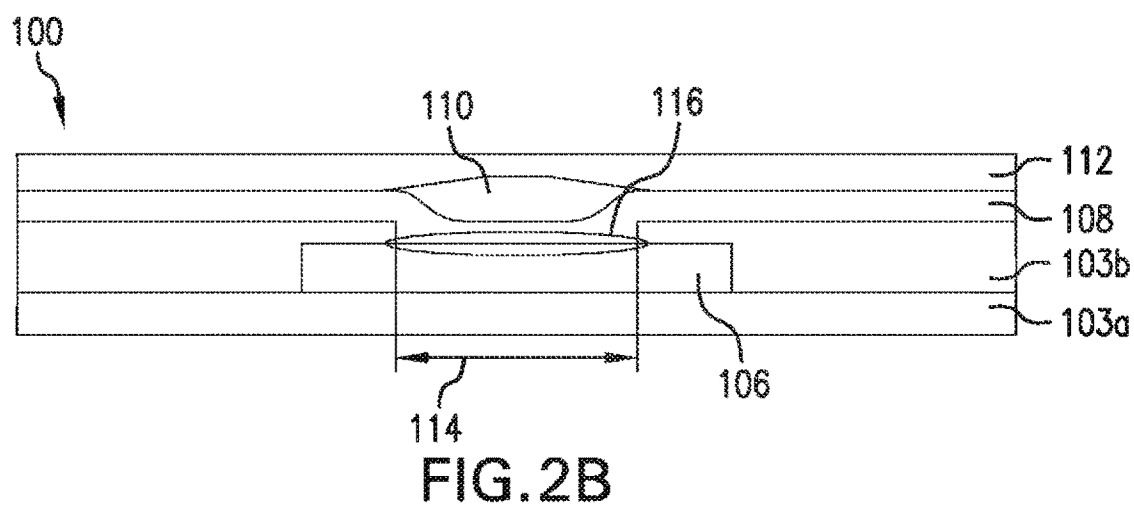
Figure 3A:
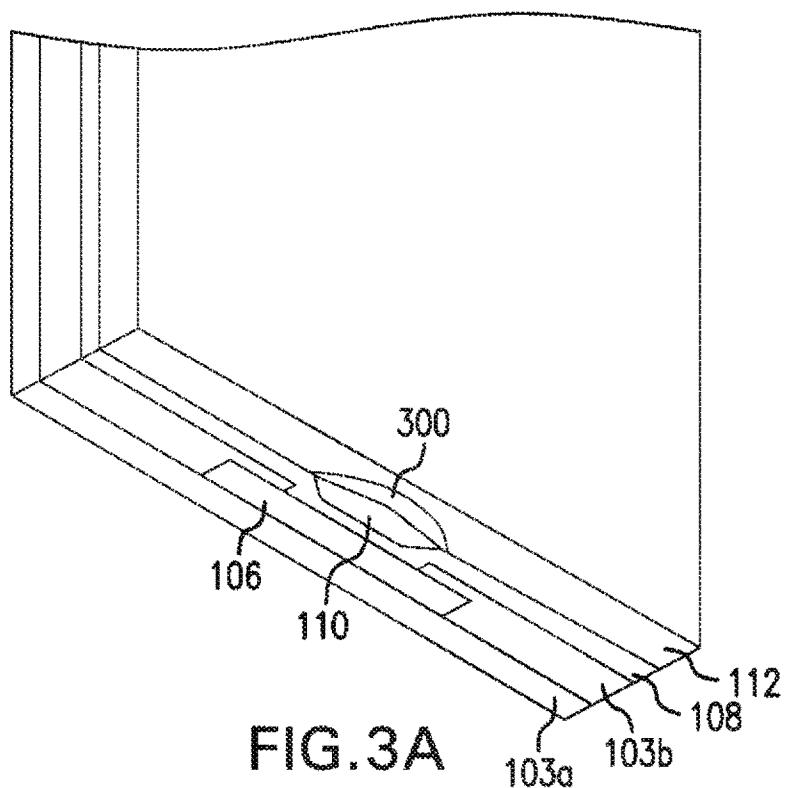
Figure 3B:
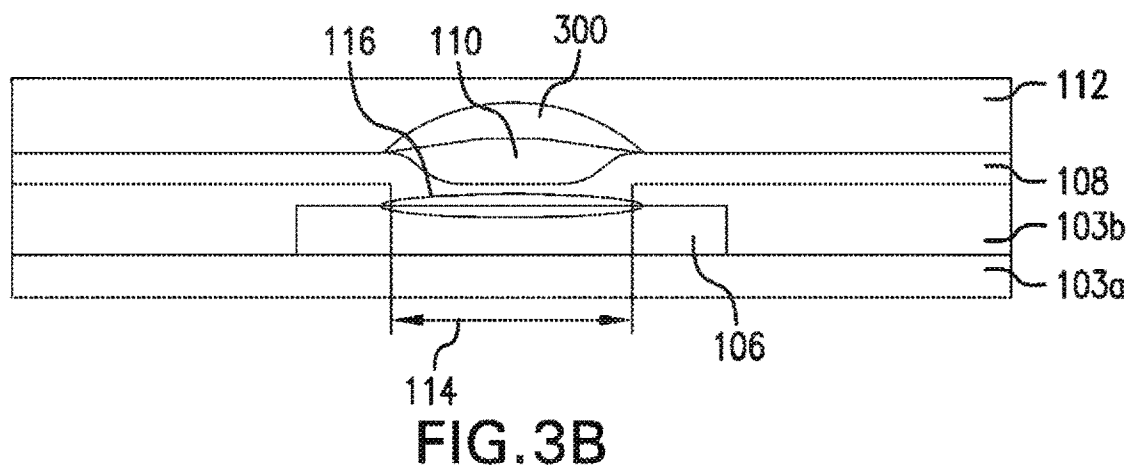
Figure 4A:
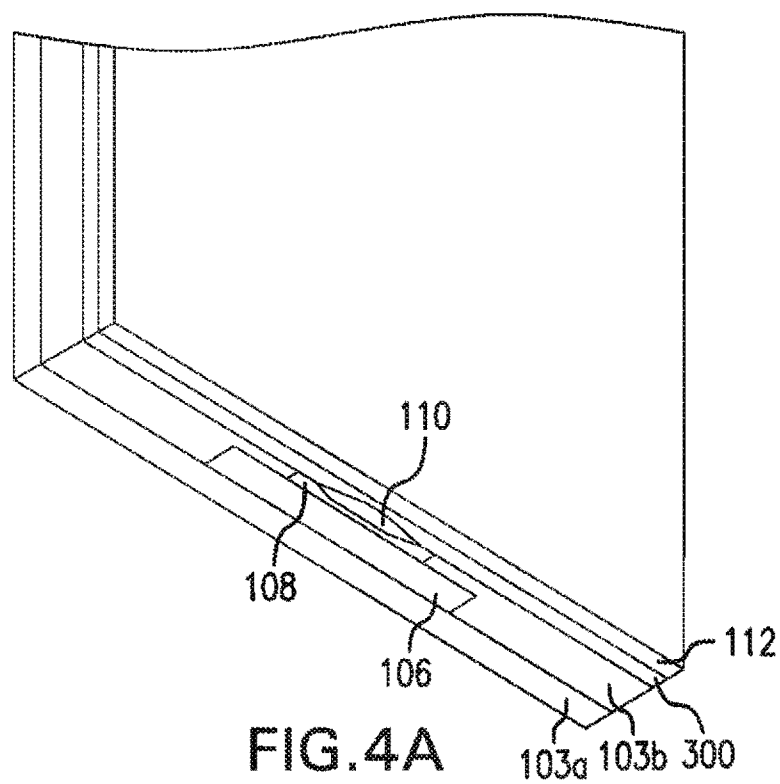
Figure 4B:
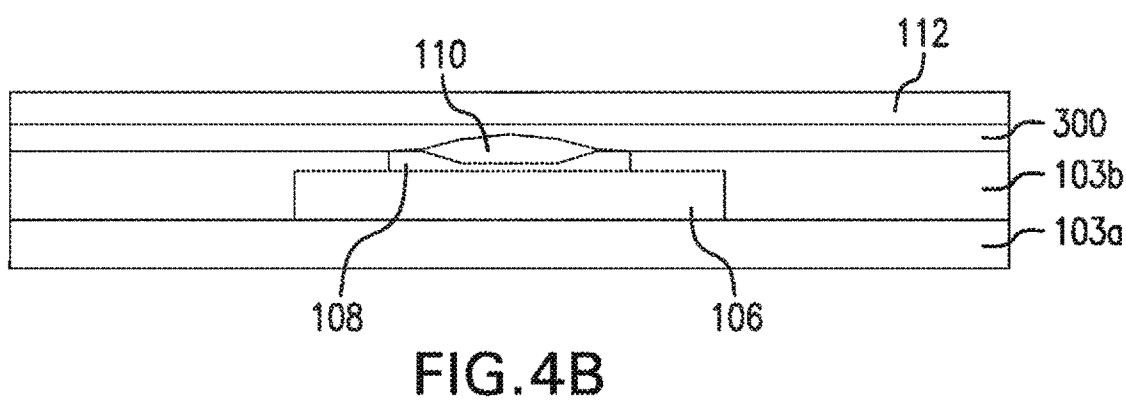
Figure 5A:
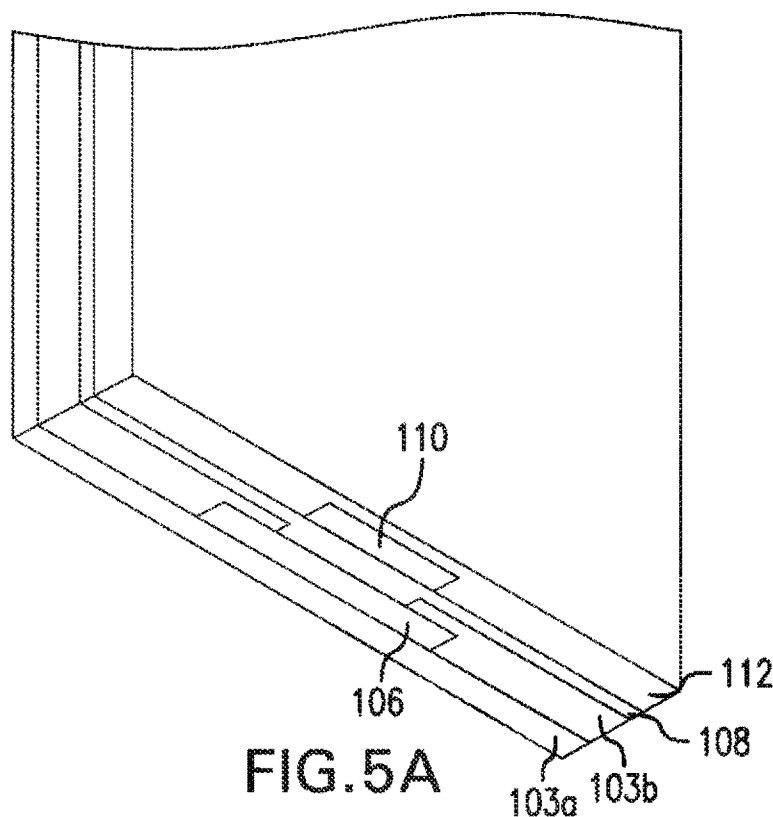
Figure 5B:
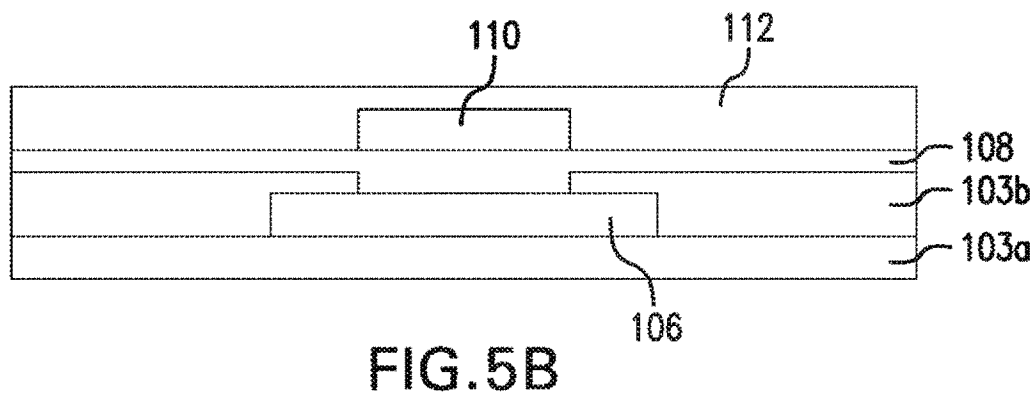
Figure 6A:
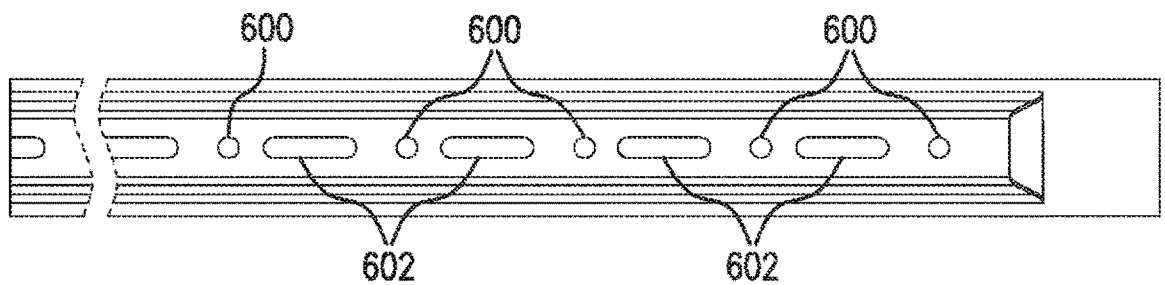
Figure 6B:
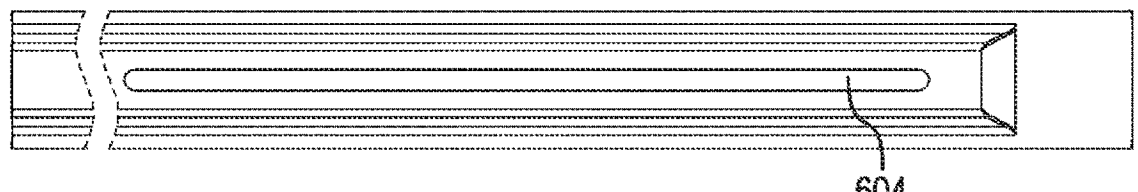

FIG. 1I is an exemplary cross-section illustrating the structure of a pseudo-reference electrode resulting from processing exposed electrode reactive surface 116 on a pseudo-reference conductor 106', in accordance with embodiments of the present invention. Two electrode function in support of a single or multi-analyte electrochemical sensor design is enabled by a uniquely designed pseudo-reference electrode, or combination counter and reference electrode. The pseudo-reference electrode is enabled by processing the electrode reactive surface 116 of a pseudo-reference conductor 106'. In one embodiment, the electrode reactive surface 116 is processed to bond with a seed layer 170. The seed layer 170 being a porous, high surface area, noble metal or electrochemically inert but electrically conductive layer that can support counter or auxiliary electrode function through aqueous electrochemical reactions. In many embodiments, the porosity of the seed layer 170 is instrumental in establishing a porous structure for subsequently applied, deposited or bonded layers.

For example, further processing bonds a reference electrode material 172 to the seed layer 170. The reference electrode material 172 enables stable interfacial potential and high exchange current density using materials such as, but not limited, to silver chloride. The reference electrode material 172 may be deposited conformally onto the seed layer 170 such that the reference electrode material 172 exhibits similar porosity to the seed layer and further enables ions present in the electrolyte to electromigrate freely between the reference electrode material 172 and the seed layer 170. In one embodiment the reference electrode material 172 is initially deposited as silver and undergoes processing to form silver/silver-chloride.

Additional processing conformally bonds a cap layer 174 to the reference electrode material 172. In many embodiments, the cap layer 172 forms a porous, high surface area, electrochemically inert layer that can support counter or auxiliary electrode function through aqueous electrochemical reactions. In many embodiments, application of the cap layer 172 creates a physically porous sandwich structure that supports ionic communication within the layers such that the half cell potential of the porous sandwich structure approximates that of silver chloride. However, the electrode reactions specific to the auxiliary or counter electrode function take place preferentially on the cap layer 172 or seed layer 170 due to low impedance of the electrode, proximity to electrolyte, and the ability to react with electrochemically active molecules within the aqueous electrolyte such as hydrogen ion, peroxide, water, and oxygen. Directing the reactions to electrode surfaces in ohmic contact with the reference electrode material 172 prevents silver chloride from being consumed through the counter or auxiliary electrode reactions, thereby maintaining the stable interfacial potential required for stable electrochemical sensor function. The end result of processing the electrode reactive surface 116 is a processed electrode reactive surface 116'. Throughout this disclosure the term electrode reactive surface 116 should be construed as interchangeable with enhanced electrode reactive surface 116' because processing the electrode reactive surface 116 may be optionally performed with every embodiment of the floating electrode.

The specific embodiments discussed above are intended to be exemplary rather than limiting. Other embodiments of the pseudo-reference electrode can include fewer or additional layers of reference electrode material or fewer or additional layers of porous, high surface area, electrochemically inert material. Furthermore, in embodiments having additional layers, a first and second reference electrode material may be used to optimize sensor performance. Similarly, various different materials exhibiting various properties such as porosity, high surface area and electrochemical inertness can be selected and placed in specific orders to tune performance of a pseudo-electrode for a particular application.

FIG. 1J is an exemplary sensor assembly 100 illustrating ionic flux 184*a* and 184*b* between a working electrode within an array of working electrodes 102 and the pseudo-reference electrode formed on side 182*b*, in accordance with embodiments of the present invention. The sensor assembly 100 includes the distal end 101*b* along with contact pad 180*a* that enables electrical connection to working electrodes 102 formed on side 182*a*. In one embodiment, contact pad 180*b* enables electrical connection to a pseudo-reference electrode formed on side 182*b*. Operationally, ions generated by the array of working electrodes 102 must travel from the working electrodes 102 through the body interface to the pseudo-reference electrode on side 182*b*. In many embodiments, the exo-sensor pathway taken by ions between the working and pseudo-reference electrode is substantially different than ionic flux generated by GLM based sensors.

In embodiments utilizing hydrogel for the first transport material, the hydrogel pathway is not constricted by overlying membranes like GLM which are designed to broadly restrict molecular flux. Without the GLM, the hydrogel pathways enables electromigration in a manner that minimizes voltage drop encountered in a two-electrode system. The minimization of voltage drop eliminates the need for voltage drop compensation, a feature more readily achieved with traditional three-electrode systems. An additional benefit of the exo-sensor current flux is the ability to use the current flux to assay the body fluid surrounding the sensor assembly 100. Intentionally creating discontinuities in the hydrogel pathway invites body fluids to bridge the path for ionic transport between electrodes. This further reduces the likelihood for voltage drop and further enables conductance measurements through an ionic pathway that is influenced, and thereby provides a measure of body fluid conductance or osmolality. Measurements of fluid conductance or osmolality in turn can be used for, but are not limited to, monitoring health status changes in the body, or to provide useful diagnostics specific to sensor implant and sensor functional integrity.

In other multi-analyte embodiments, rather than singular contact pad 180*a*, multiple contact pads can be formed that correspond to the number of analytes being measured. Additionally, while single contact pad 180*b* may be sufficient for a pseudo-reference electrode, different embodiments can optionally use a discrete counter electrode and a discrete reference electrode. In these embodiments, contact pad 180*b* may be divided into a plurality of contact pads that correspond with the number of electrodes formed on side 182*b*.

Figure 2A:
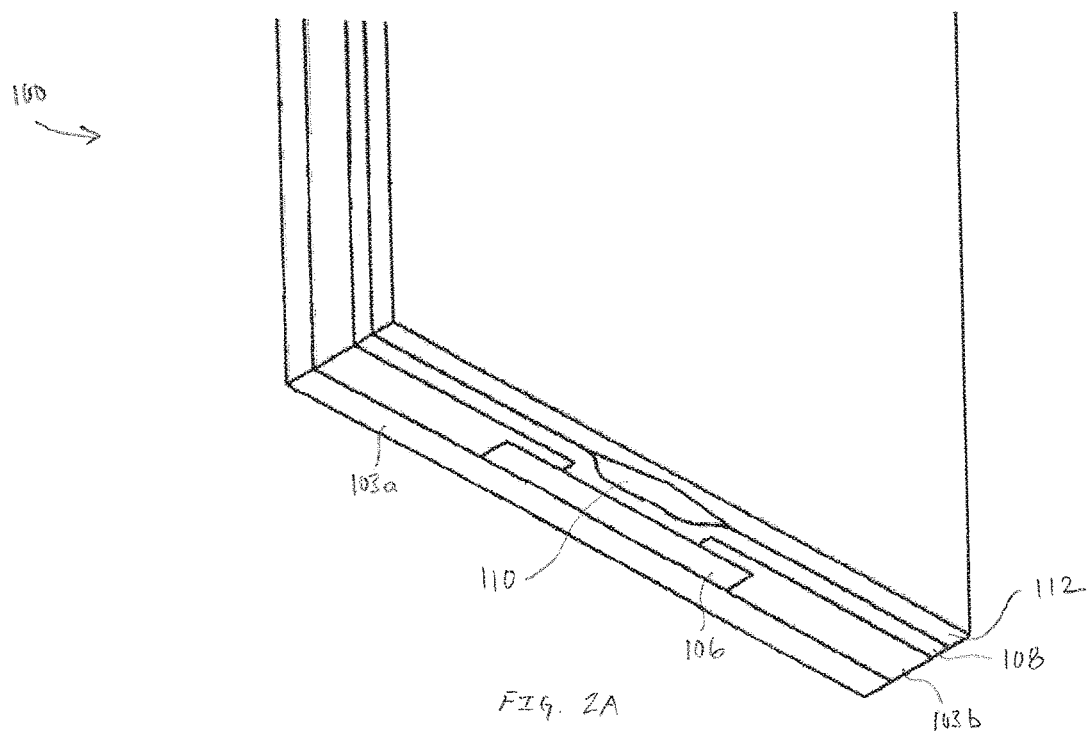
FIGS. 2A and 2B are respectively, a pseudo-isometric view of an exemplary cross-section of an electrode and a cross-section view of the exemplary electrode illustrated in FIG. 2A, in accordance with embodiments of the present invention.
Figure 2B:
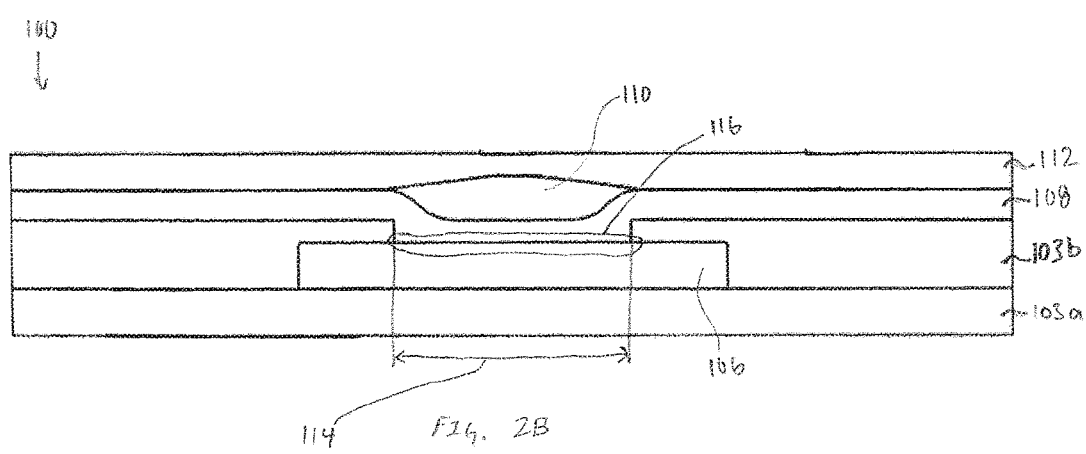

FIGS. 2A and 2B are respectively, a pseudo-isometric view of an exemplary cross-section of an electrode 102 and a cross-section view of the exemplary electrode illustrated in FIG. 2A, in accordance with embodiments of the present invention. The embodiment illustrated in FIGS. 2A and 2B includes a combined layer of insulation 103*a* and adhesive adjacent to the working conductor 106. The working conductor 106 having an electrode reactive surface 116 enabled by opening 114 within insulation 103*b*. Covering the entirety of the both the insulation 103*b* and the electrode reactive surface 116 is the first transport material 108. Differentiating the embodiment in FIG. 2A from the embodiment in FIG. 1A is the placement of the first reactive chemistry 110 substantially over the exposed reactive surface 116 but not extending substantially beyond the edges of the opening 114. The first reactive chemistry 110 is sandwiched between the first transport material 108 and the second transport material 112.

Figure 3A:
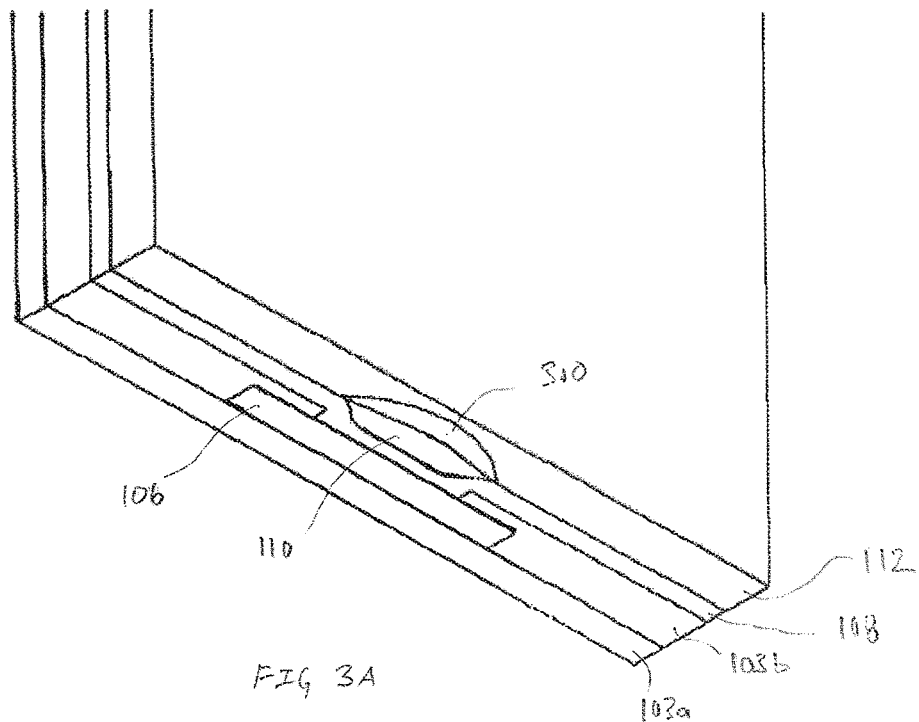
FIGS. 3A and 3B are respectively, a pseudo-isometric view of an exemplary cross-section of an electrode and a cross-section view of the exemplary electrode illustrated in FIG. 3A, in accordance with embodiments of the present invention.
Figure 3B:
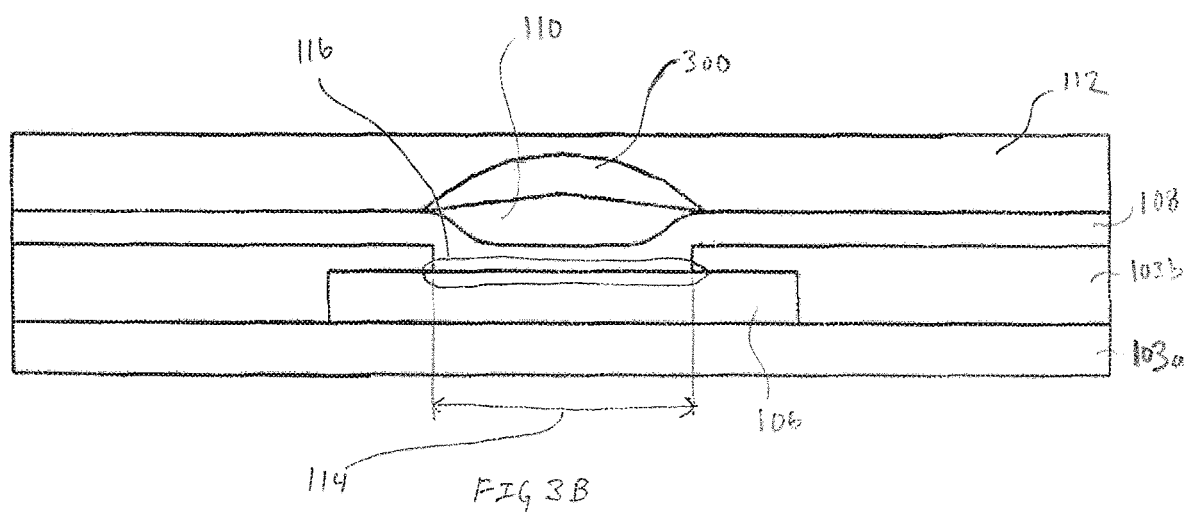

FIGS. 3A and 3B are respectively, a pseudo-isometric view of an exemplary cross-section of an electrode 102 and a cross-section view of the exemplary electrode illustrated in FIG. 3A, in accordance with embodiments of the present invention. The embodiments illustrated in FIG. 3A includes second reactive chemistry 300. In many embodiments, the second reactive chemistry 300 is similar to the first reactive chemistry in that it can be a mixture, blend or suspension of a hydrogel and a compound/molecule that has desirable properties within the electrode. In embodiments where the electrode is based on a enzymatic reaction that produces hydrogen peroxide that is intended to be consumed on the working conductor, it may be beneficial to control the amount of hydrogen peroxide using catalase or peroxidase.

For example, in an embodiment where the analyte being measured by the electrode is lactate, the first reactive chemistry 110 can be lactate oxidase. The first transport material enables diffusion of lactate to the first reactive chemistry 110 where it reacts and produces the by-product hydrogen peroxide that is consumed on the electrode reactive surface 116. However, in some instances, excessive amounts of lactate can produce an excess of hydrogen peroxide that cannot be effectively reduced on the electrode reactive surface 116. Additionally, the over production of hydrogen peroxide can have a negative effect on the lactate oxidase. To mitigate the excessive amount of hydrogen peroxide, the second reactive chemistry can be selected from a family of catalase or peroxidase both of which consume hydrogen peroxide.

Figure 4A:
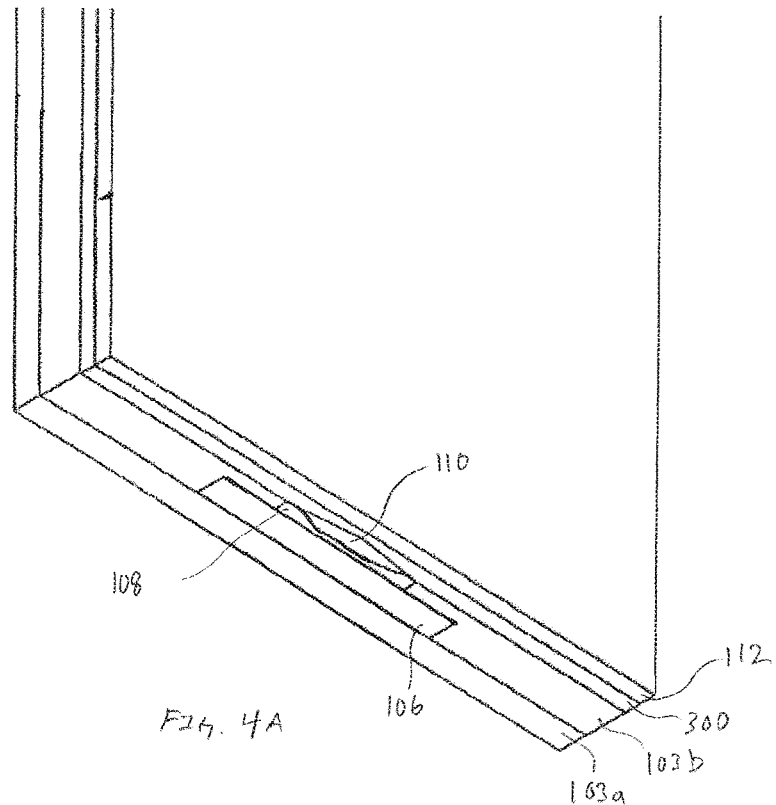
FIGS. 4A and 4B are respectively, a pseudo-isometric view of an exemplary cross-section of an electrode and a cross-section view of the exemplary electrode illustrated in FIG. 4A, in accordance with embodiments of the present invention.
Figure 4B:
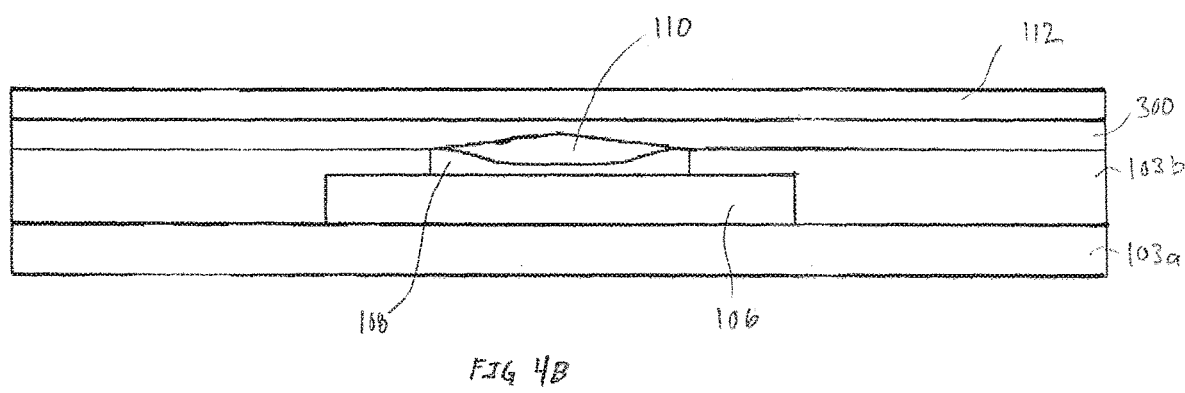

FIGS. 4A and 4B are respectively, a pseudo-isometric view of an exemplary cross-section of an electrode and a cross-section view of the exemplary electrode illustrated in FIG. 4A, in accordance with embodiments of the present invention. In FIGS. 4A and 4B the second reactive chemistry 300 is applied across the top of the first reactive chemistry 110. Furthermore, the first reactive chemistry is separated from the electrode reactive surface 116 by a layer of first transport material 108. Because the second reactive chemistry 300 can be a mixture, blend, or suspension of a desirable molecule/compound within a hydrogel, the entire layer of second reactive chemistry 300, applied to the edge of the sensor assembly, can supply analyte or other biorecognition molecules to the first reactive chemistry. Exemplary embodiments utilizing the configuration illustrated in FIGS. 4A and 4B include, but are not limited to instances where the second reactive chemistry operates as an interference rejection layer. When used as interference rejection layer, the nomenclature of second reactive chemistry may technically be a misnomer in that the second reactive chemistry may not technically react so much as reject specific molecules or compounds. For example, in some embodiments, the second reactive chemistry may be electrically charged to repel or attract specific molecules/compounds. In other embodiments, the second reactive chemistry can be blended or mixed using a hydrogel selected based properties of restricting or limiting diffusion of specific molecules or compounds. Alternatively, the embodiment shown in FIGS. 4A and 4B may also be used to control production of hydrogen peroxide as described in FIGS. 3A and 3B.

Figure 5A:
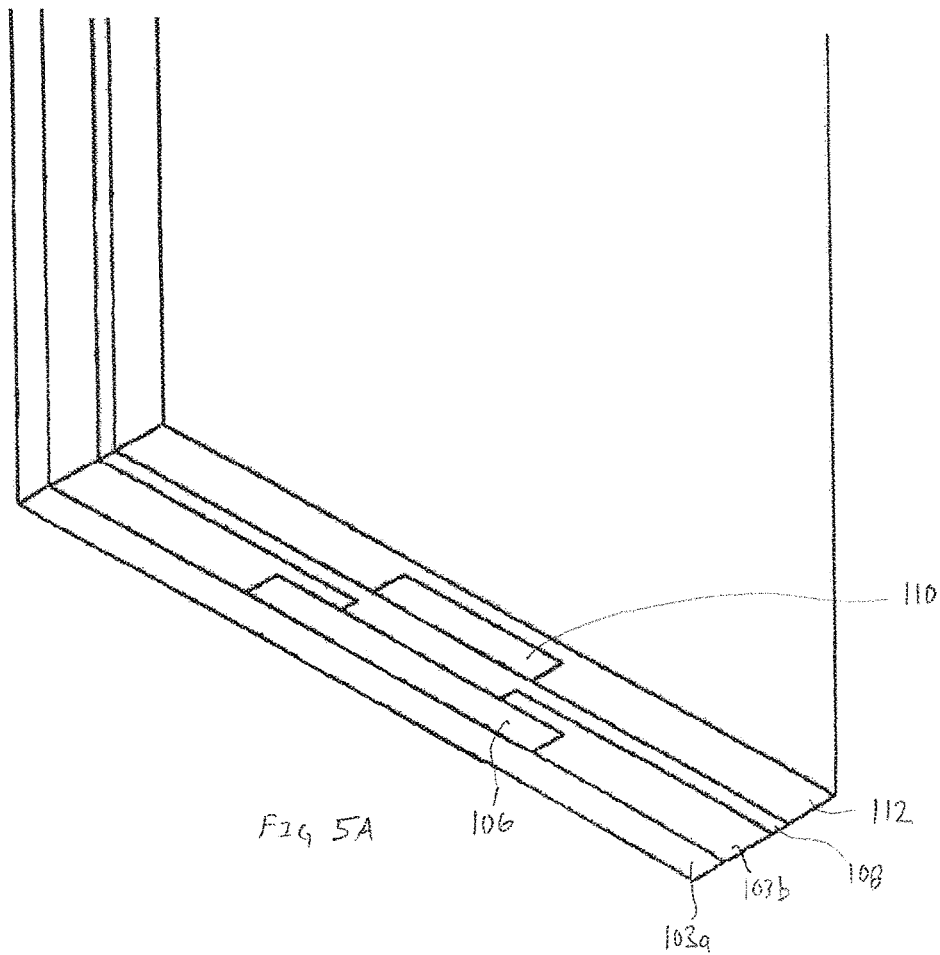
FIGS. 5A and 5B are respectively, a pseudo-isometric view of an exemplary cross-section of an electrode and a cross-section view of the exemplary electrode illustrated in FIG. 5A, in accordance with embodiments of the present invention.
Figure 5B:
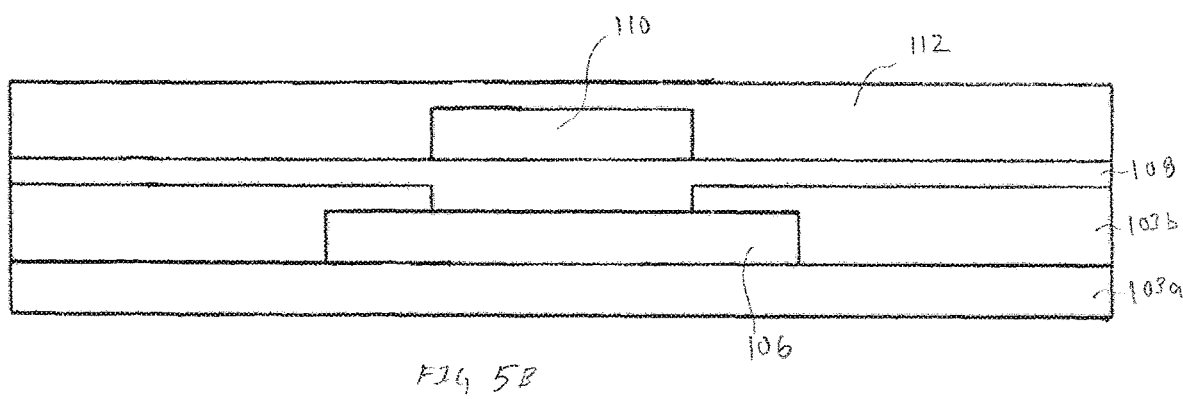

FIGS. 5A and 5B are respectively, a pseudo-isometric view of an exemplary cross-section of an electrode and a cross-section view of the exemplary electrode illustrated in FIG. 5A, in accordance with embodiments of the present invention. This embodiment eschews the conformal application of the first reactive chemistry 110. While this embodiment can reduce the surface area for analyte within the first transport material 108 to interact with the first reactive chemistry 110, depending on the analyte being measured, it may be desirable to reduce the area to create first reactive chemistry 110 by-products. Additionally, while the application of the first reactive chemistry 110 is illustrated as being substantially coincident with the opening 114, in other embodiments, the first reactive chemistry 110 extends beyond the opening 114 to more effectively shadow the opening 114. Furthermore, in as much as physically possible, the features of the various embodiments discussed throughout the disclosure should be construed as interchangeable or combinable with other embodiments discussed herein.

Figure 6A:
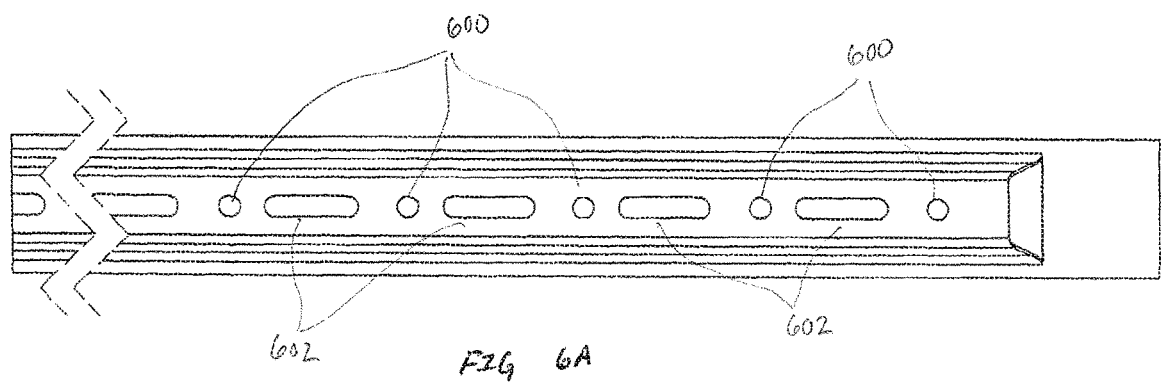
FIGS. 6A and 6B are exemplary alternative embodiments of sensor assemblies utilizing different configurations of electrode shapes, in accordance with embodiments of the present invention.
Figure 6B:
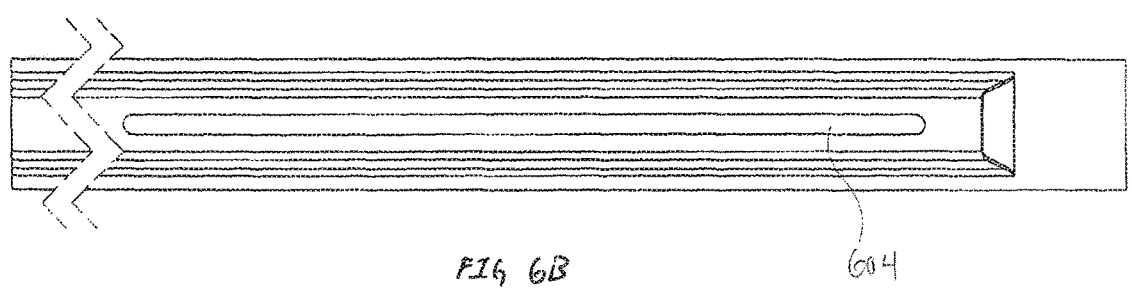

FIGS. 6A and 6B are exemplary alternative embodiments of sensor assemblies 102 utilizing different configurations of electrode shapes, in accordance with embodiments of the present invention. While the discrete separate electrodes shown and discussed in FIGS. 1A and 1B may have benefits, various other configurations of openings can be used to create floating electrodes or pseudo-reference electrodes. FIG. 6A is an embodiment that includes circular electrodes 600 with oval electrodes 602. FIG. 6B is an exemplary illustration of an embodiment utilizing a monolithic oval electrode 604 that may be similar in appearance to traditional planar electrodes while retaining the operational advantages of a floating electrode. Alternatively, the shapes of the electrodes 600, 602, and 604 shown in either 6A or 6B could be used to make pseudo-reference electrodes. The examples provided are intended to be exemplary rather than limiting as changes can be made to the shape, aspect-ratio and other features of the openings 114. Furthermore, various configurations of openings can be used on a single analyte or multi-analyte sensor assembly.

Figure 7:
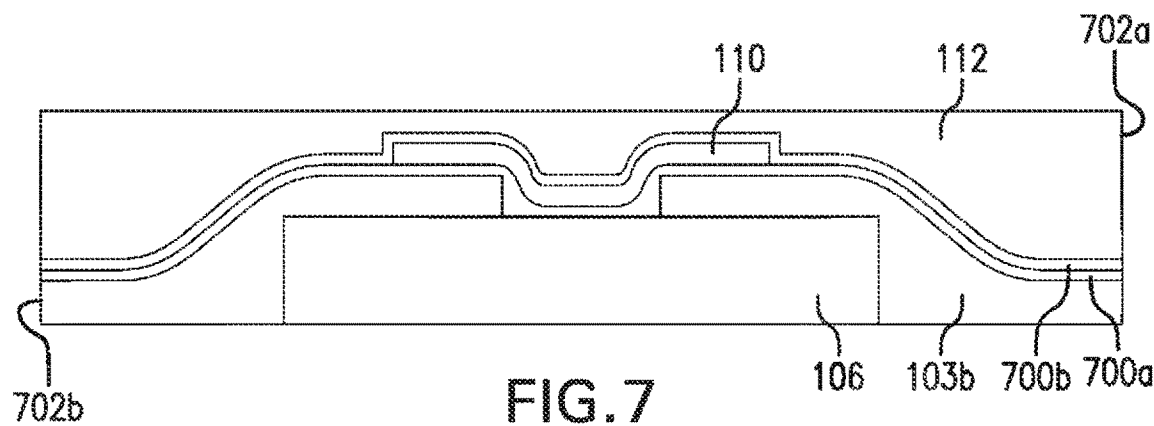
FIG. 7 is an exemplary alternative embodiment of an electrode, in accordance with embodiments of the present invention.
Figure 8:
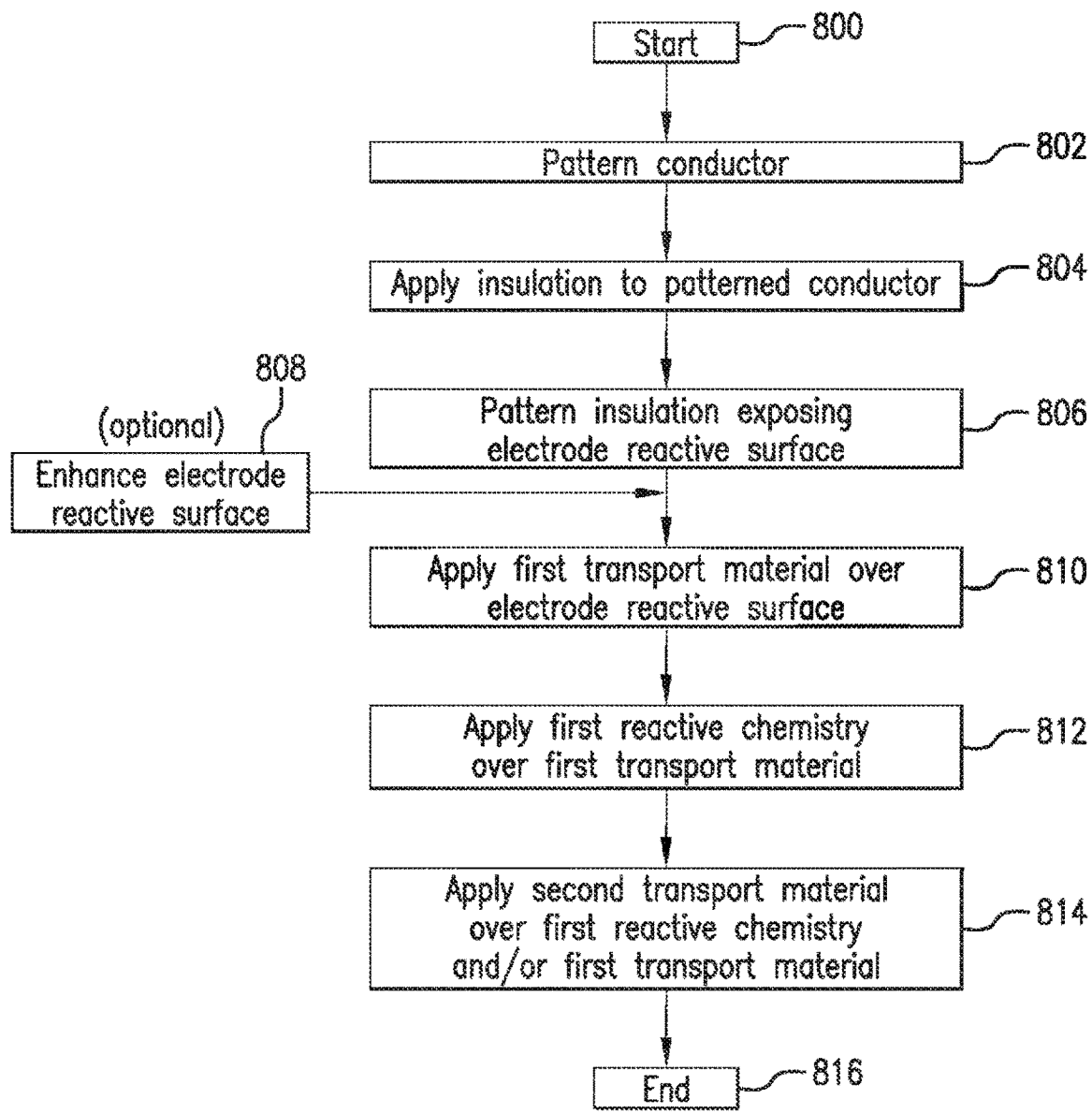
Figure 9A:
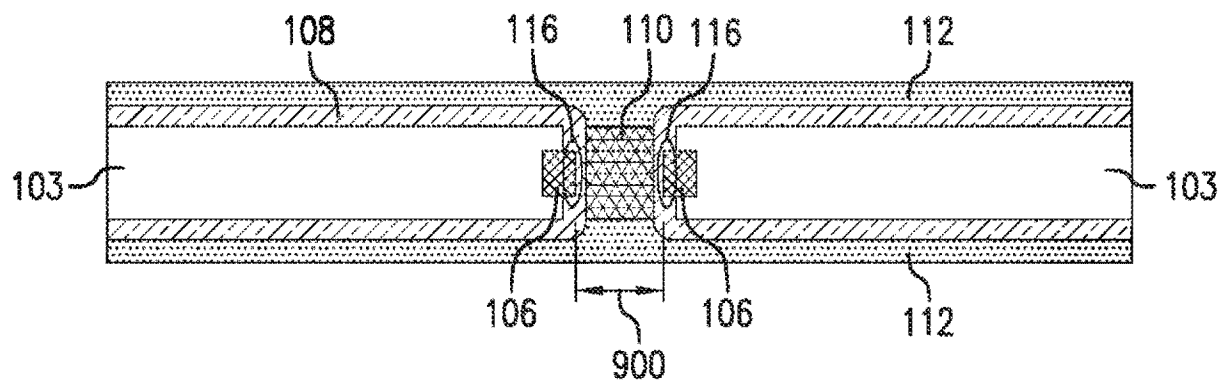
Figure 9B:
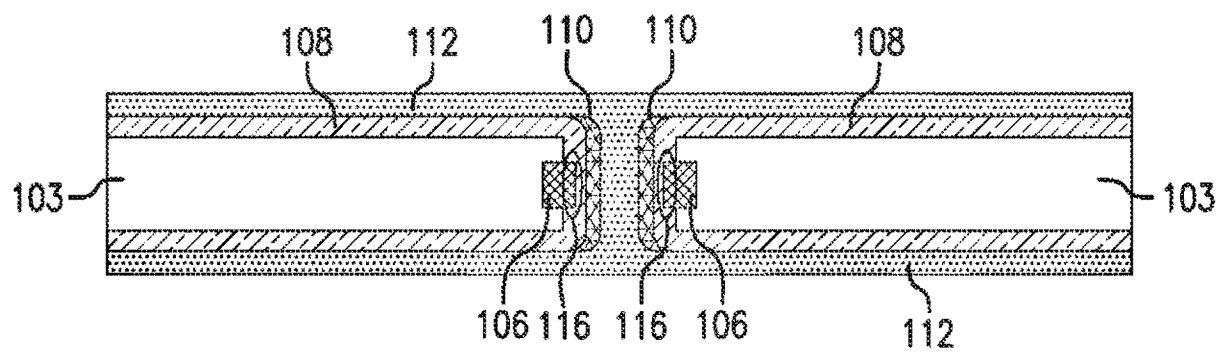
Figure 9C:
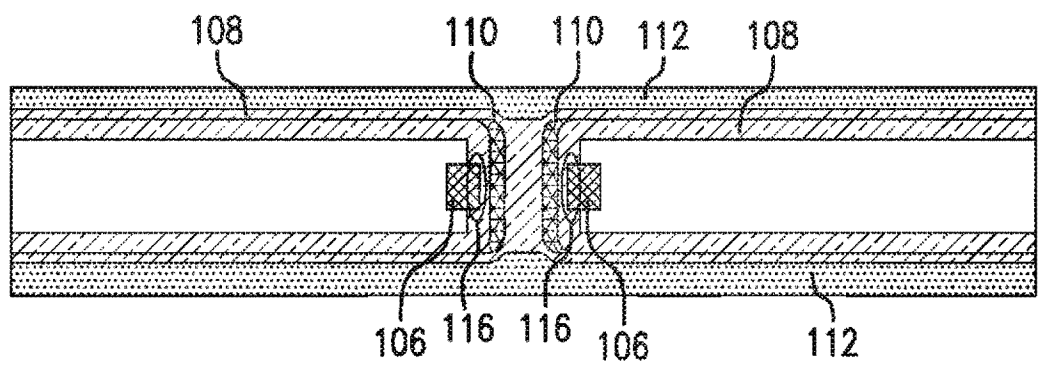

FIG. 7 is an exemplary alternative embodiment of an electrode 102, in accordance with embodiments of the present invention. Differentiating the embodiment in FIG. 7 is the encapsulation of the first reactive chemistry 110 with transport material 700a and transport material 700b before applying second transport material 112 over the multilayer structure. While FIG. 7 illustrates transport materials 700a and 700b being substantially similar in thickness, in various embodiments the transport materials can be tuned for the electrode by altering variable such as, but not limited to thickness, doping molecules, transport coefficients for different molecules including reactants supplied by the second transport materials 112 and the like. As illustrated, the increased surface area capable of sustaining analyte/first reactive chemistry reactions is greatly enhanced. The increased surface area for enzymatic reactions and the like may be useful for electrodes configured to measure analyte or biomarkers that are found in extremely low concentrations. The embodiment shown in FIG. 7 is intended to be exemplary. In other embodiments that include multiple transport materials, each of the respective transport materials can be selectively applied so as to cover select portions or the entirety of the sensor assembly. For example, as illustrated in FIG. 7, the transport material 700b extends between edges 702a and 702b. In alternate embodiments, the transport material 700b may be selectively applied over the first reactive chemistry 110 and not extend to edges 702a and 702b.

Figure 8:
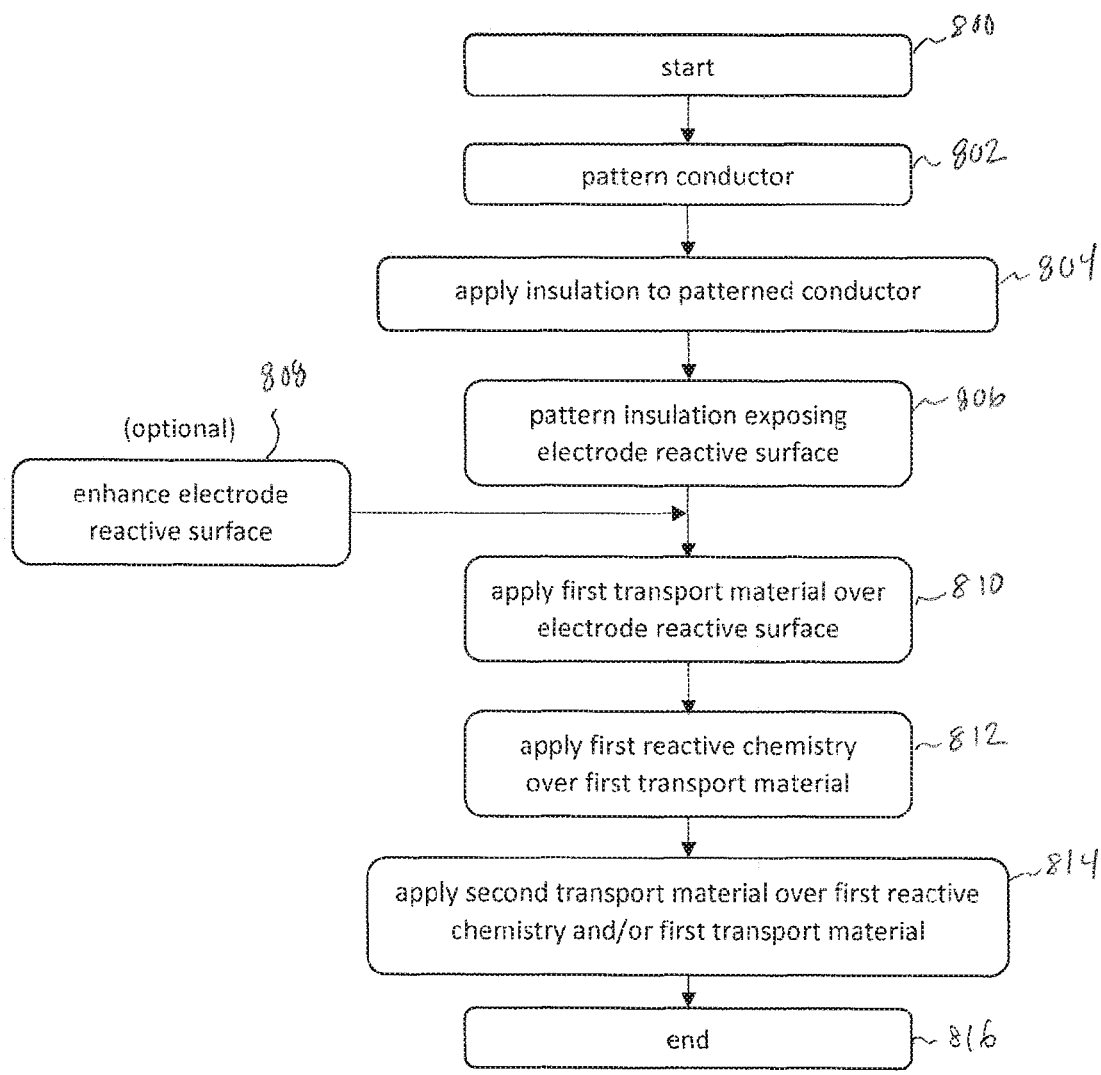
FIG. 8 is an exemplary flowchart with operations to create a floating electrode, in accordance with embodiments of the present invention.

FIG. 8 is an exemplary flowchart with operations to create a floating electrode, in accordance with embodiments of the present invention. The flowchart begins with start operation 800. Operation 802 patterns a conductor which in some embodiments is a sheet of stainless steel. The patterning of the conductor defines the working electrodes along with other structures of the sensor assembly, such as, but not limited to a counter electrode, reference electrode, or even a combined counter-reference electrode. Operation 804 applies insulation to the patterned conductor. In some embodiments the insulation applied in operation 804 is applied to both sides of the patterned conductor. In other embodiments, the patterned conductor includes insulation on one side resulting in operation 804 applying insulation to only a single side.

Operation 806 patterns insulation covering the patterned conductor thereby exposing the electrode reactive surface. As previously discussed, the patterning of the insulation creates the openings in the insulation that will eventually be shadowed by the first reactive chemistry. While many of the embodiments in the present disclosure are illustrated as circular openings, the openings in the insulation can be any shape, including, but not limited to triangles, squares, other polygons, ovals, or combinations thereof. Optional operation 808 enhances the electrode reactive surface. In many embodiments operation 808 electroplates the electrode reactive surface with electrochemical enhancing properties such as, but not limited to silver, silver/silver-chloride, platinum black or combinations thereof.

Operation 810 applies the first transport material over the electrode reactive surface. As illustrated in many embodiments, the first transport material blankets the entire surface of the sensor assembly. In many embodiments, the first transport material is a hydrogel at least partially selected based on its ability to enable diffusion of the analyte being measured. Accordingly, edge-to-edge coverage of the sensor assembly with the first transport material enables analyte to enter the sensor and the first transport material sustains diffusion of the analyte into the electrode. Additionally, the first transport material enables diffusion of a by-product of a reaction between the analyte and the first reactive chemistry to the electrode reactive surface.

Operation 812 applies the first reactive chemistry over the first transport material. In many embodiments the first reactive chemistry is a blend, mixture or suspension of a reactive molecule or compound with a hydrogel. In many embodiments the hydrogel selected to make the first reactive chemistry is the same as the first transport material. In other embodiments, a hydrogel other than the first transport material is used to make the first reactive chemistry. While many of the embodiments discussed utilized discrete, selective placement of the first reactive chemistry over the exposed electrode reactive surface, blanket coating or partially blanket coating the surface of the first transport material with the first reactive chemistry should not be construed as beyond the scope of this disclosure. Accordingly, operation 814 applies a second transport material over the first reactive chemistry or, a combination of the first reactive chemistry and the first transport material. In many embodiments the second transport material is selected based on criteria such as, but not limited to, ability to supply reactant to the first reactive chemistry, hydrophobicity, and impermeability to the analyte being measured. It may be desirable for the second transport material to be impervious to diffusion of the analyte because it can create a no flux boundary that confines diffusion of the analyte within the first transport material.

The operations discussed above are intended to be exemplary rather than comprehensive. Additional or fewer operations can be performed that result in an identical or similar structure. The specific embodiment enabled by the operations discussed above should also not be construed as limiting. Rather, the application of additional transport materials may be desirable or necessary to effectively transport various analytes to different portions of the sensor assembly. For example, in an embodiment of a multianalyte sensor assembly a first transport material may be applied at a first thickness to enable efficient transport of a first analyte to a first electrode array that has a first reactive chemistry. Also placed on the same sensor assembly is a second transport material having a second thickness that enables efficient transport of a second analyte to a second electrode array having a different biorecognition ability than the first reactive chemistry. In some embodiments multiple transport materials may be preferred or required. However, in many embodiments a single transport material may be selected that enables concentration gradients to be established for a plurality of analytes to the different reactive chemistries.

A significant benefit of the floating electrode design is the ability to generate a response concomitant with Fick's law of diffusion for two different molecules/analytes within a body at two different concentrations using shared materials such as a shared first transport material. Patterning multiple working conductors on a single sensor assembly can enable multianalyte functionality that requires selective masking and application of different reactive chemistries to different working conductors. To accomplish similar multianalyte performance using traditional limiting membranes may require the use of a limiting membrane specific to each analyte being measured.

Figure 9A:
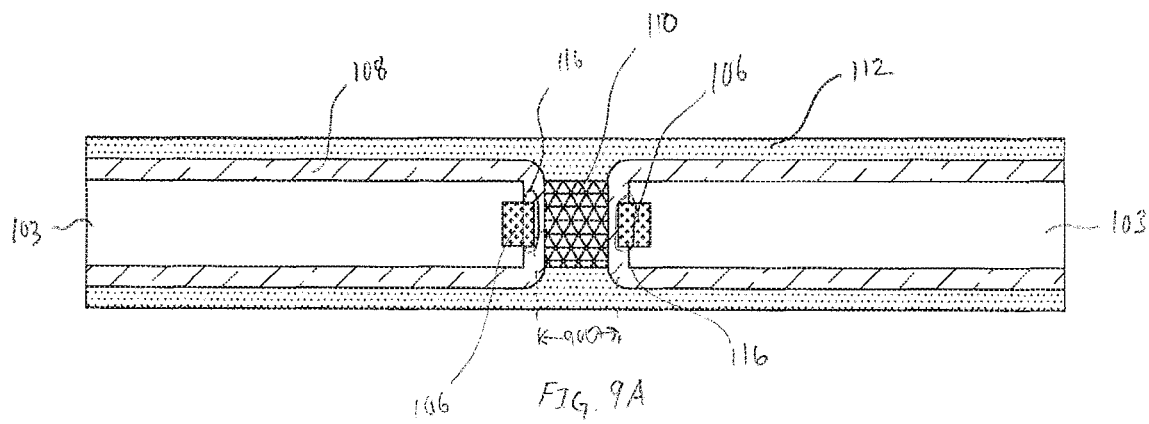
FIGS. 9A-9C are exemplary cross-section illustrations of various embodiments of an aperture electrode that utilize the concept of a floating electrode, in accordance with embodiments of the present invention.
Figure 9B:
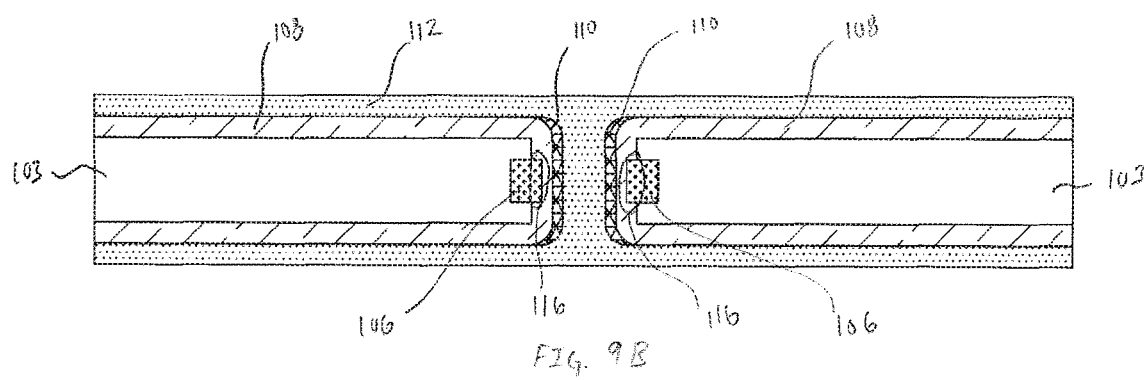
Figure 9C:
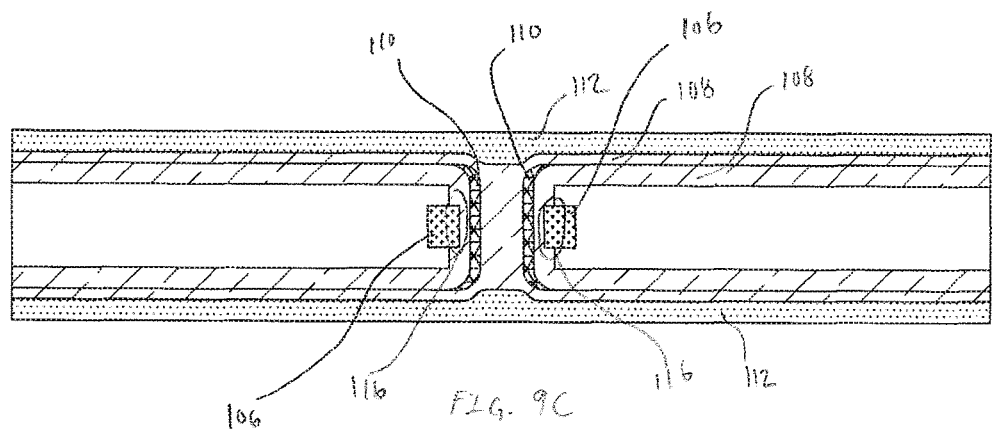

FIGS. 9A-9C are exemplary cross-section illustrations of different embodiments of an aperture electrode that utilize the concept of a floating electrode, in accordance with embodiments of the present invention. The operational concepts of the floating electrode can be applied to the basic concepts of the aperture sensor that is described in U.S. patent application Ser. No. 15/472,194, filed Mar. 28, 2017, titled "ANALYTE SENSOR", which is herein incorporated by reference in its entirety. The cross-sections shown in FIGS. 9A-9C are of an individual electrode within an array of like or dissimilar electrodes that make up the sensor assembly 100. The embodiment shown in FIG. 9A includes a working conductor 106 that includes an aperture 900. In many embodiments the aperture 900 is a circular hole formed in the working conductor 106. Surrounding the majority of the working conductor 106 is insulation 103. In many embodiments insulation 103 will be composed of multiple layers of material, but for simplicity, insulation 103 is illustrated as a monolithic layer. First transport material 108 is applied over the insulation 103 and remainder of the exposed working conductor 106. Similar to the embodiments shown and described in FIGS. 1B-1D, the working electrode 106 includes the electrode reactive surface 116. In each embodiment shown in FIGS. 9A-9C, the electrode reactive surface 116 is separated from the first reactive chemistry 110 by first transport material 108 thereby separating the oxidoreductase reaction between the analyte being measured and the oxidation of the byproducts of the oxidoreductase on the electrode reactive surface 116.

Further replicating the operational structure of the floating electrode, in each of the embodiments in FIGS. 9A-9C, the analyte being measured is restricted to diffusion through the first transport material 108 because the first transport material is encapsulated by the analyte impervious, or analyte impermeable, second transport material 112. Additionally, the second transport material 112 is in contact with the first reactive chemistry 110, thereby enabling efficient transfer of necessary reactants or cofactors, such as, but not limited to oxygen.

While the description above refers to particular embodiments of the present invention, it will be understood that many modifications may be made without departing from the spirit thereof. It is intended that the various embodiments and features of floating electrodes can be combined or mixed with other embodiments such as the aperture electrode, and boss electrode disclosed in U.S. patent application Ser. No. 15/472,194, filed Mar. 28, 2017 to create a vast variety of robust sensor assemblies ranging from single analyte with different types or working electrodes to multiple analyte with like or dissimilar types of working electrodes. The particular examples provided are intended to be illustrative embodiments of the multitude of combinations possible. Additionally, while the disclosure has compared the floating electrode design to those using GLM, it may be possible to use GLM or other limiting membranes as part of a floating electrode design. Furthermore, the specific theories of operation provided throughout the disclosure should not be considered limiting. Rather, the disclosure is being made without being bound by any particular theory of operation. Accordingly, the disclosed embodiments and associated theories of operation are intended to be considered in all respects as illustrative and not restrictive.

The invention claimed is:

1. An analyte sensor, comprising:
a working conductor having an electrode reactive surface;
a first reactive chemistry being responsive to a first analyte;
a first transport material that enables flux of the first analyte to the first reactive chemistry through an exposed lateral edge of the first transport material; and
a second transport material disposed over and configured to supply a reactant to the first reactive chemistry,
wherein the first reactive chemistry does not contact the electrode reactive surface while at least partially shadowing a portion of the electrode reactive surface, the first reactive chemistry not extending to the exposed lateral edge.

2. The analyte sensor described in claim 1, wherein the first reactive chemistry is located between the first transport material and the second transport material.

3. The analyte sensor described in claim 1, wherein a first by-product is the product of the first analyte reacting with the first reactive chemistry.

4. The analyte sensor in claim 3, wherein the first transport material enables flux of the first byproduct to the electrode reactive surface.

5. The analyte sensor described in claim 4, wherein the second transport material extends to the exposed lateral edge.

6. The analyte sensor described in claim 1, wherein the first transport material is applied over and in contact with the electrode reactive surface.

7. The analyte sensor described in claim 1, wherein the second transport material is impermeable to the first analyte.

8. The working electrode described in claim 1, wherein the first transport layer further enables flux of the reactant supplied by the second transport material.

9. An analyte sensor, comprising:
- a working conductor having an electrode reactive surface;
- a first reactive chemistry being responsive to a first analyte;
- a first transport material including one or more exposed surfaces configured to enable flux of the first analyte from a biomarker containing fluid to pass directly from the biomarker containing fluid into the first transport material and to the first reactive chemistry; and
- a second transport material including one or more exposed surfaces configured to enable a reactant from the biomarker containing fluid to pass directly from the biomarker containing fluid into the second transport material and to the first reactive chemistry.

10. The analyte sensor of claim 9, wherein the first transport material is disposed over and directly in contact with the electrode reactive surface.

11. The analyte sensor of claim 10, wherein the first reactive chemistry is disposed over and directly in contact with the first transport material.

12. The analyte sensor of claim 11, wherein the first reactive chemistry laterally overlaps the electrode reactive surface and is not in contact with the electrode reactive surface.

13. The analyte sensor of claim 12, wherein the second transport material is disposed over and directly in contact with both the first reactive chemistry and the first transport material.

14. The analyte sensor of claim 13, wherein the second transport material is impermeable to the first analyte.

15. An analyte sensor, comprising:
- a working conductor having an electrode reactive surface;
- a first reactive chemistry being responsive to a first analyte;
- a first transport material that enables flux of the first analyte to the first reactive chemistry; and
- a second transport material supplying a reactant to the first reactive chemistry,
- wherein the first reactive chemistry is sandwiched by the first transport material and the second transport material, the first and second transport material being in direct contact with one another in an area laterally outside of the first reactive chemistry.

16. The analyte sensor of claim 15, wherein the first transport material is disposed over the electrode reactive surface.

17. The analyte sensor of claim 16, wherein the first reactive chemistry is disposed over and is directly in contact with the first transport material.

18. The analyte sensor of claim 17, wherein the first reactive chemistry laterally overlaps the electrode reactive surface.

19. The analyte sensor of claim 15, wherein the first reactive chemistry is not in contact with the electrode reactive surface.

20. The analyte sensor of claim 19, wherein the second transport material is impermeable to the first analyte.

* * * * *

UNITED STATES PATENT AND TRADEMARK OFFICE
CERTIFICATE OF CORRECTION

PATENT NO. : 11,553,862 B2
APPLICATION NO. : 16/625884
DATED : January 17, 2023
INVENTOR(S) : Rajiv Shah et al.

It is certified that error appears in the above-identified patent and that said Letters Patent is hereby corrected as shown below:

In the Drawings

Please replace Figs. 1A-1J, 2A, 2B, 3A, 3B, 4A, 4B, 5A, 5B, 6A, 6B, 7, 8, 9A-9C with the concurrently filed 15 pages of replacement sheets.

The replacement sheets do not introduce new matter.

Signed and Sealed this
Twentieth Day of June, 2023

Katherine Kelly Vidal
*Director of the United States Patent and Trademark Office*